US010653491B2

(12) United States Patent
Lathrop et al.

(10) Patent No.: US 10,653,491 B2
(45) Date of Patent: *May 19, 2020

(54) DEXTEROUS SURGICAL MANIPULATOR AND METHOD OF USE

(71) Applicant: Vanderbilt University, Nashville, TN (US)

(72) Inventors: Ray A. Lathrop, Nashville, TN (US); Robert J. Webster, III, Nashville, TN (US); James Netterville, Nashville, TN (US); Arundathi Prasad, Zionsville, IN (US); Stanley Duke Herrell, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 179 days.

This patent is subject to a terminal disclaimer.

(21) Appl. No.: 15/874,239

(22) Filed: Jan. 18, 2018

(65) Prior Publication Data
US 2018/0140369 A1 May 24, 2018

Related U.S. Application Data

(63) Continuation of application No. 13/460,497, filed on Apr. 30, 2012, now Pat. No. 9,901,412.
(Continued)

(51) Int. Cl.
*A61B 34/00* (2016.01)
*A61B 17/29* (2006.01)

(52) U.S. Cl.
CPC ............ *A61B 34/70* (2016.02); *A61B 34/71* (2016.02); *A61B 17/29* (2013.01);
(Continued)

(58) Field of Classification Search
CPC ............ A61B 17/00234; A61B 17/29; A61B 17/2909; A61B 2017/003;
(Continued)

(56) References Cited

U.S. PATENT DOCUMENTS 4,315,650 A 2/1982 Yoshida
5,286,228 A 2/1994 Lee et al.
(Continued)

FOREIGN PATENT DOCUMENTS

CN 1438097 8/2003
CN 2917558 7/2007
(Continued)

OTHER PUBLICATIONS

Diks, J. et al., "The mechanical master-slave manipulator: an instrument improving the performance in standardized asks for endoscopic surgery," Surgical Endoscopy, vol. 21, No. 6 1025-1031 (Jun. 2007).
(Continued)

*Primary Examiner* — Robert A Lynch
(74) *Attorney, Agent, or Firm* — Michael Best & Friedrich LLP

(57) ABSTRACT

A surgical manipulator includes an internal working end having an internal joint, and an external control interface linked to the internal working end for controlling the internal working end. The external control interface includes at least one lever defining a grip volume for a surgeon's hand when gripping and operating the at least one lever, and an external joint linked to the internal joint for controlling the internal joint. The external joint is positioned substantially within the grip volume.

20 Claims, 17 Drawing Sheets

Related U.S. Application Data

(60) Provisional application No. 61/481,038, filed on Apr. 29, 2011.

(52) U.S. Cl.
CPC . *A61B 2017/291* (2013.01); *A61B 2017/2908* (2013.01); *A61B 2017/2919* (2013.01); *A61B 2017/2927* (2013.01); *A61B 2017/2947* (2013.01); *A61B 2034/715* (2016.02)

(58) Field of Classification Search
CPC ........... A61B 2017/00305; A61B 2017/00318; A61B 2017/00323; A61B 2017/00336; A61B 2017/2908; A61B 2017/2909; A61B 2017/291; A61B 2017/2919; A61B 2017/2927; A61B 2017/2947; A61B 34/70; A61B 34/71
See application file for complete search history.

(56) References Cited

U.S. PATENT DOCUMENTS

| | | | |
|---|---|---|---|
| 5,370,658 A * | 12/1994 | Scheller | A61B 17/2909 606/174 |
| 5,468,250 A | 11/1995 | Paraschac et al. | |
| 5,599,151 A | 2/1997 | Daum et al. | |
| 5,813,813 A | 9/1998 | Daum et al. | |
| 5,928,263 A | 7/1999 | Hoogeboom | |
| 6,299,625 B1 | 10/2001 | Bacher | |
| 6,322,578 B1 | 11/2001 | Houle et al. | |
| 6,398,726 B1 | 6/2002 | Ramans et al. | |
| 7,090,637 B2 | 8/2006 | Danitz et al. | |
| 7,372,229 B2 | 5/2008 | Farritor et al. | |
| 7,373,219 B2 | 5/2008 | Nowlin et al. | |
| 7,386,365 B2 | 6/2008 | Nixon | |
| 7,404,716 B2 | 7/2008 | Gregorio et al. | |
| 7,410,483 B2 | 8/2008 | Danitz et al. | |
| 8,105,350 B2 | 1/2012 | Lee et al. | |
| 8,617,203 B2 | 12/2013 | Stefanchik et al. | |
| 2006/0020288 A1 | 1/2006 | Leonard | |
| 2007/0225754 A1 | 9/2007 | Measamer et al. | |
| 2008/0065106 A1 | 3/2008 | Larkin | |
| 2008/0071288 A1 | 3/2008 | Larkin et al. | |
| 2008/0071290 A1 | 3/2008 | Larkin et al. | |
| 2008/0071291 A1 | 3/2008 | Duval et al. | |
| 2008/0140129 A1 | 6/2008 | Dalton | |
| 2010/0198253 A1 | 8/2010 | Jinno et al. | |
| 2010/0298864 A1 | 11/2010 | Castro | |
| 2011/0106145 A1 * | 5/2011 | Jeong | A61B 17/29 606/205 |
| 2012/0143173 A1 | 6/2012 | Steege et al. | |

FOREIGN PATENT DOCUMENTS

| | | |
|---|---|---|
| CN | 101011292 | 8/2007 |
| DE | 102006007107 | 8/2007 |
| WO | 2008041227 | 4/2008 |

OTHER PUBLICATIONS

Jaspers, Joris, "Cheaper and Simpler Keyhole Surgery," Delft University of Technology (Mar. 21, 2006) http://www.tudelft.org/en/current/latest-news/article/detail/kjkoperaties-goedkoper-en-eenvoudiger/.

Bhaheetharan, Sujan et al., "Minimally Invasive Surgery Tool," http://homepages.cae.wiscedu/~bme200/robotic_arm_fall05/reports/BME_mid_sem_report.pdf (Oct. 18, 2005).

Humphries, Courtney, "New Tools for Minimally Invasive Surgery," Technology Review Published by MIT (Aug. 9, 2006) http://www.technologyreview.com/read_article.aspx?id=17279&ch=biotech&a=f.

"Minimally invasive heart surgery research wins $5 million NIH award," Children's Hospital Boston News Room, Sep. 5, 2007 http://childrenshospital.org/newsroom/Site1339/mainpageS1339P340.html.

"Startup's device may change surgery," The News & Observer (Jan. 8, 2008) http://satellite.tmcnet.com/news/2008/01/08/3200080.htm.

"Trends in the noninvasive and minimally invasive medical device market," BCC Research (Jun. 2006) http://www.surgicenteronline.com/articles/751feat3.html.

Ethicon Endo-Surgery Inc., http://www.ethiconendo.com/dtcf/pages/innovative_products.htm; information available prior to Apr. 29, 2011.

Mectra Labs, Inc., About Mectra http://www.mectralabs.com/aboutMectra.cfm; information available prior to Apr. 29, 2011.

NeuroArm product, http://www.neuroarm.org/; information available prior to Apr. 29, 2011.

Zeus Robotic Surgical System, http://en.wikipedia.org/wiki/ZEUS_robotic_surgical_system; information available prior to Apr. 29, 2011.

QuadPort product, http://www.advancedsurgical.ie/QuadPort/Default.544.html; information available prior to Apr. 29, 2011.

ROBODOC product, http://www.robodoc.com/professionals.html; information available prior to Apr. 29, 2011.

Triport product, http://www.advancedsurgical.ie/TriPort_15/Default.595.html; information available prior to Apr. 29, 2011.

* cited by examiner

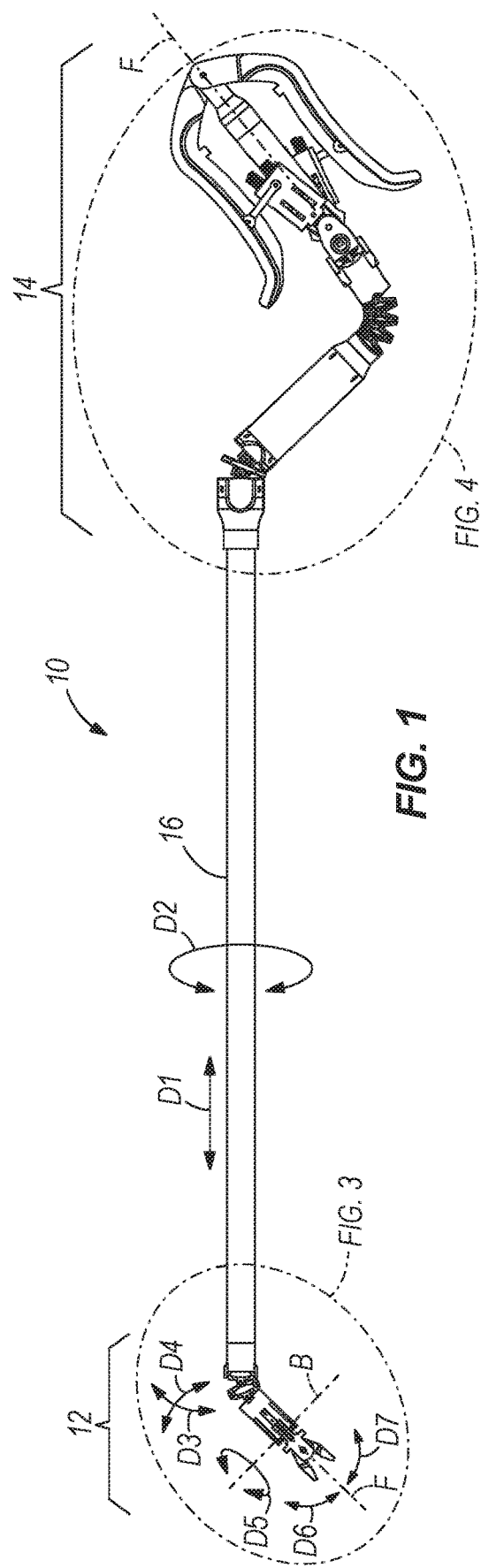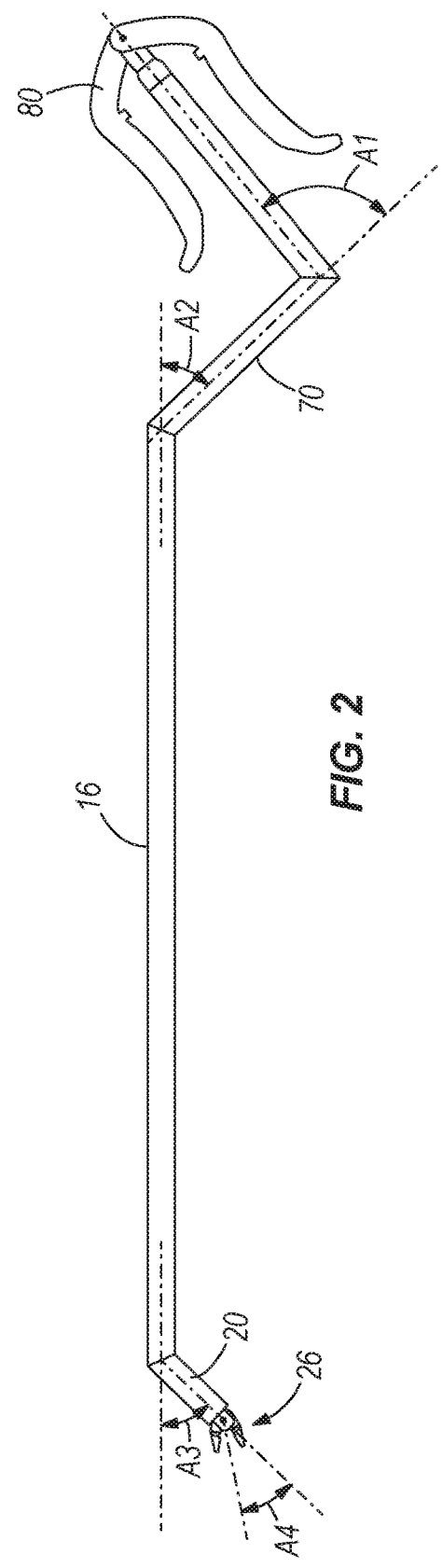

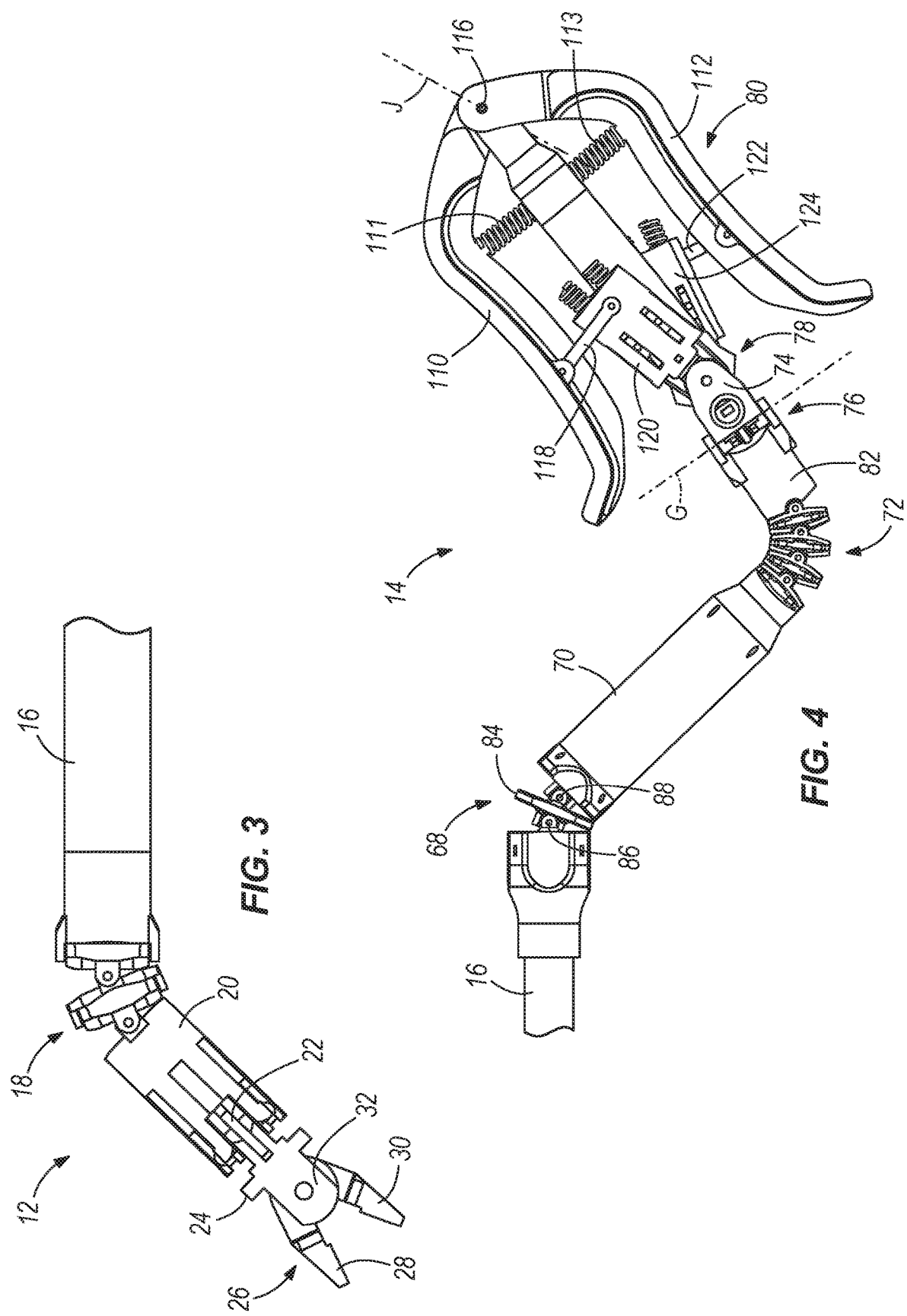

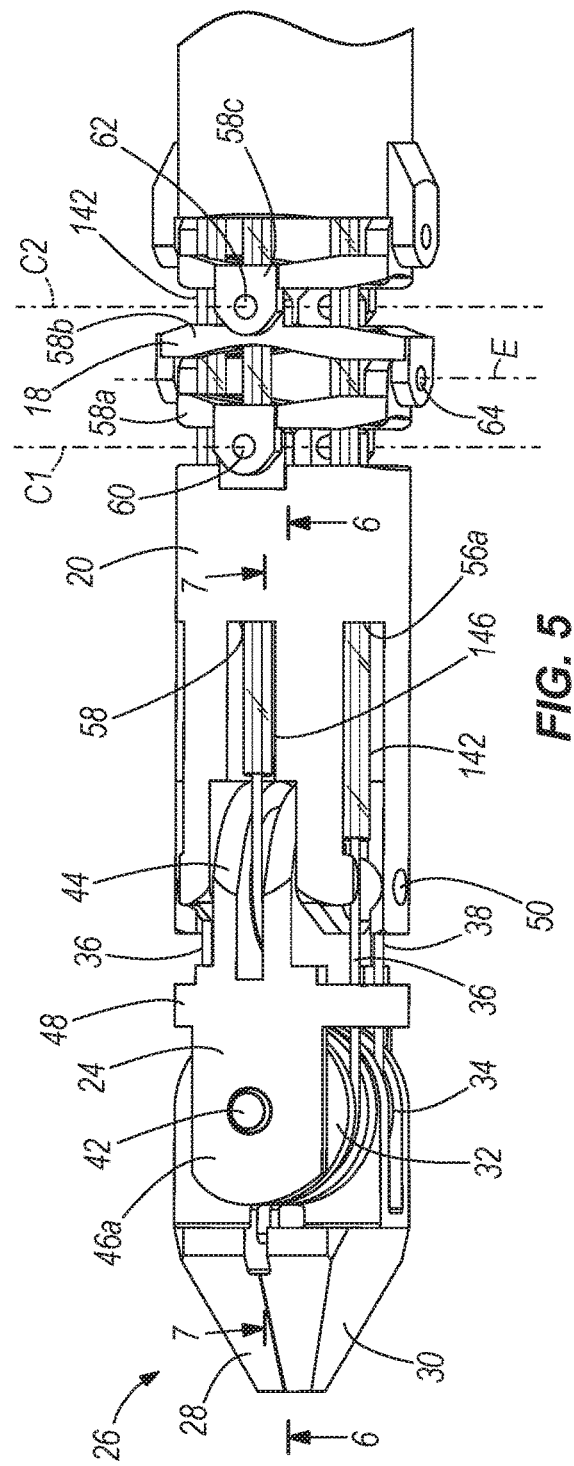
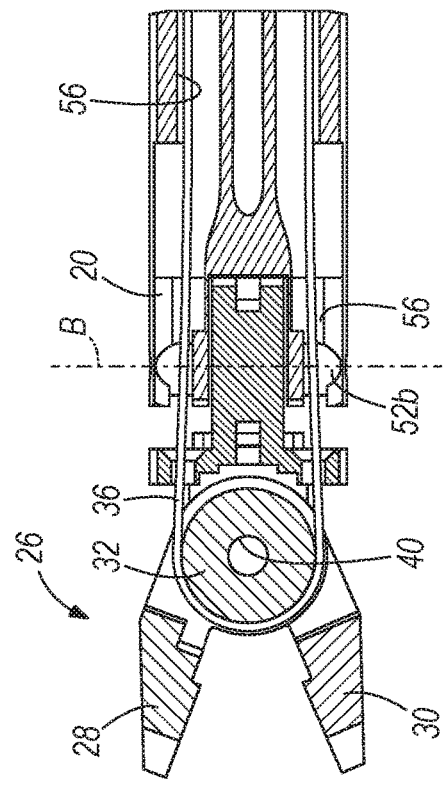
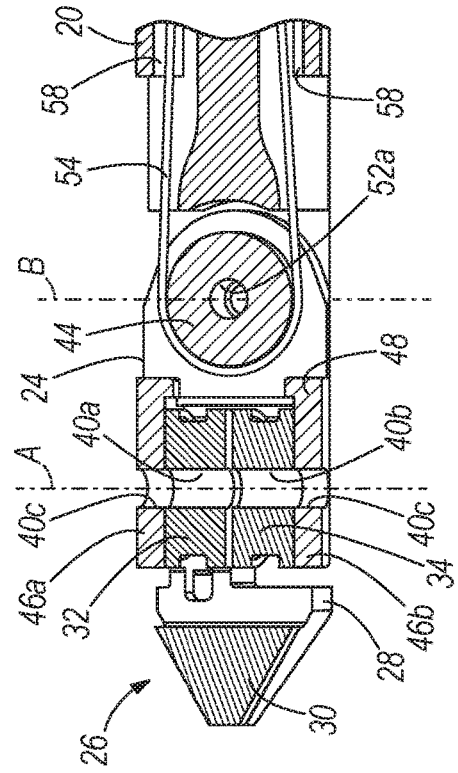

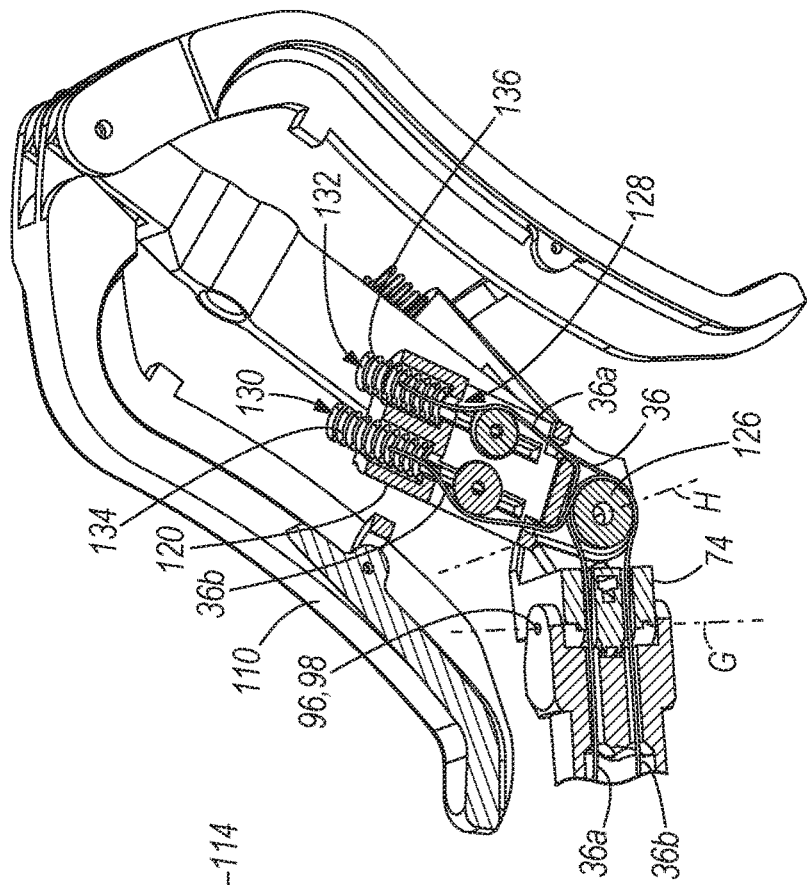
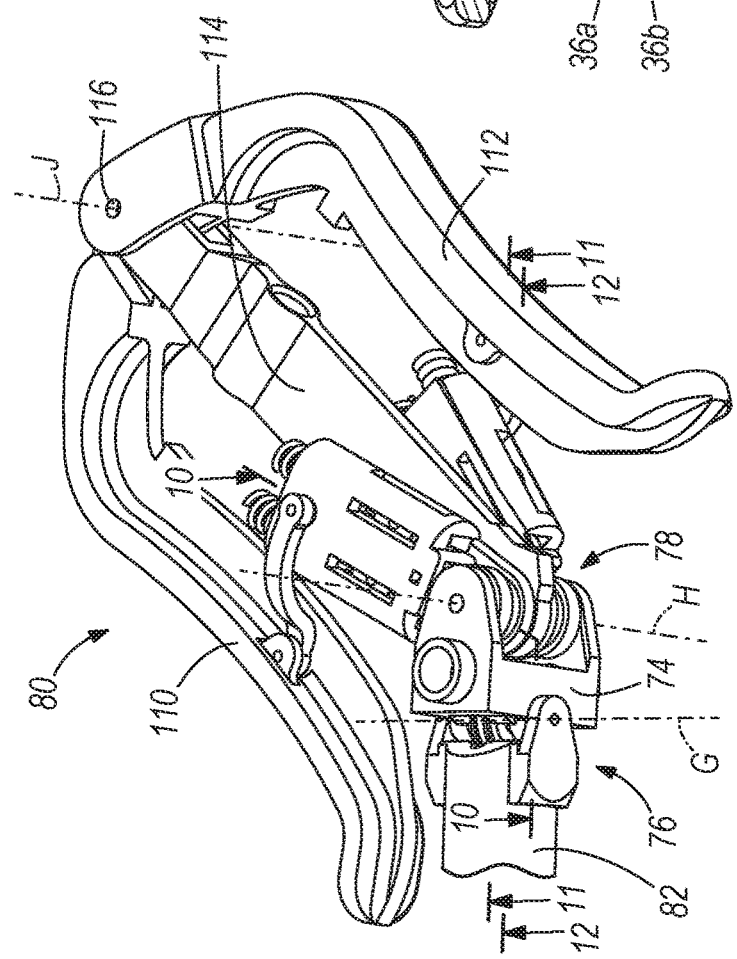

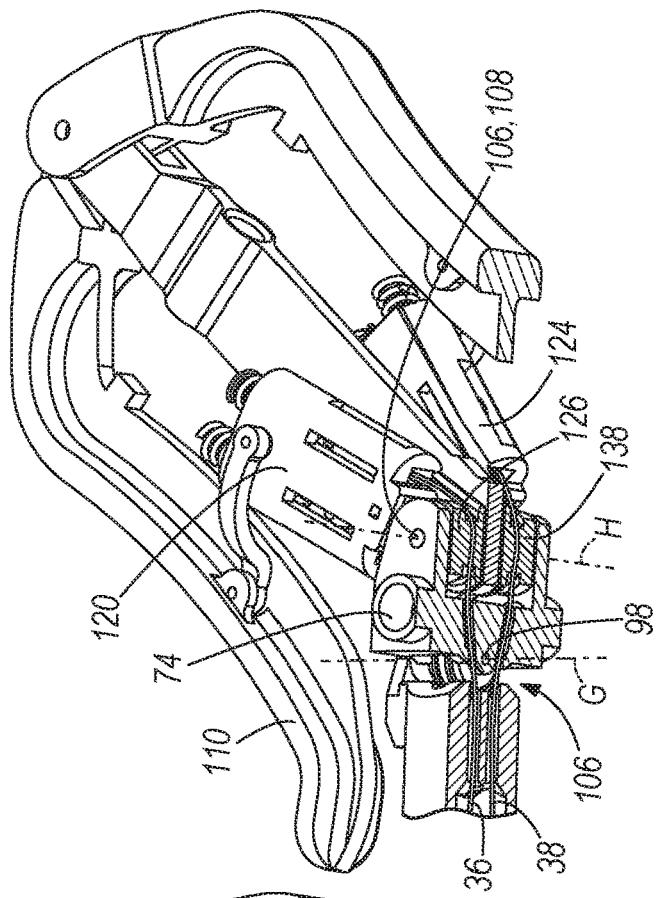
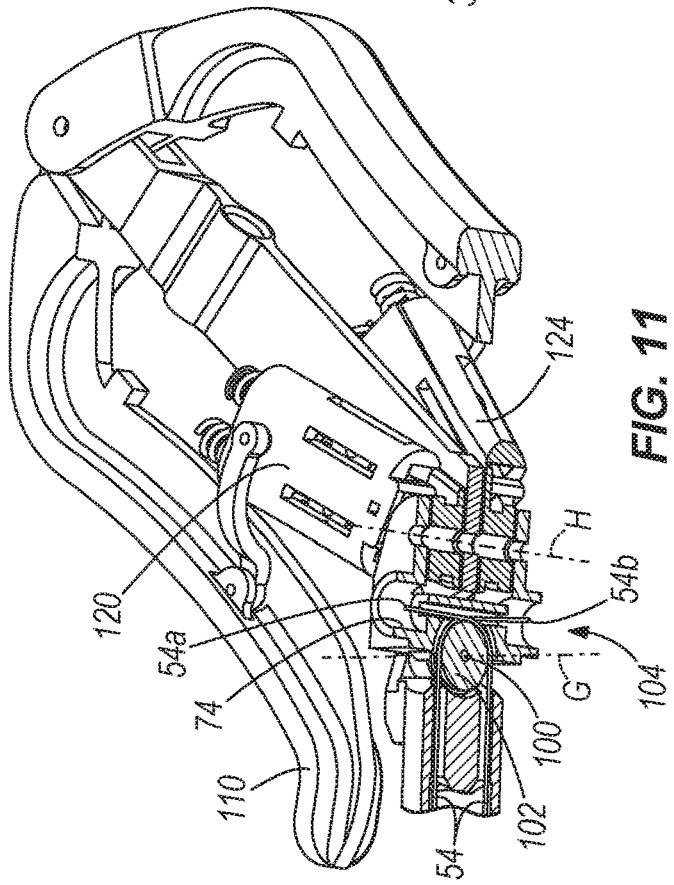

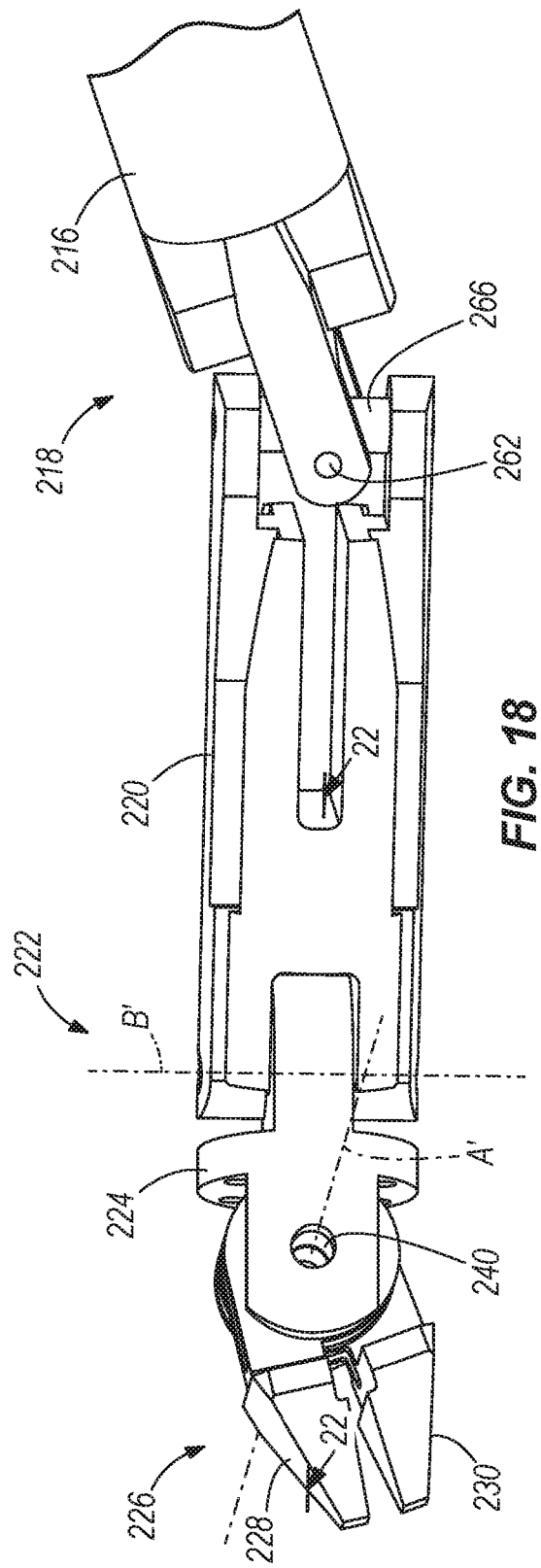
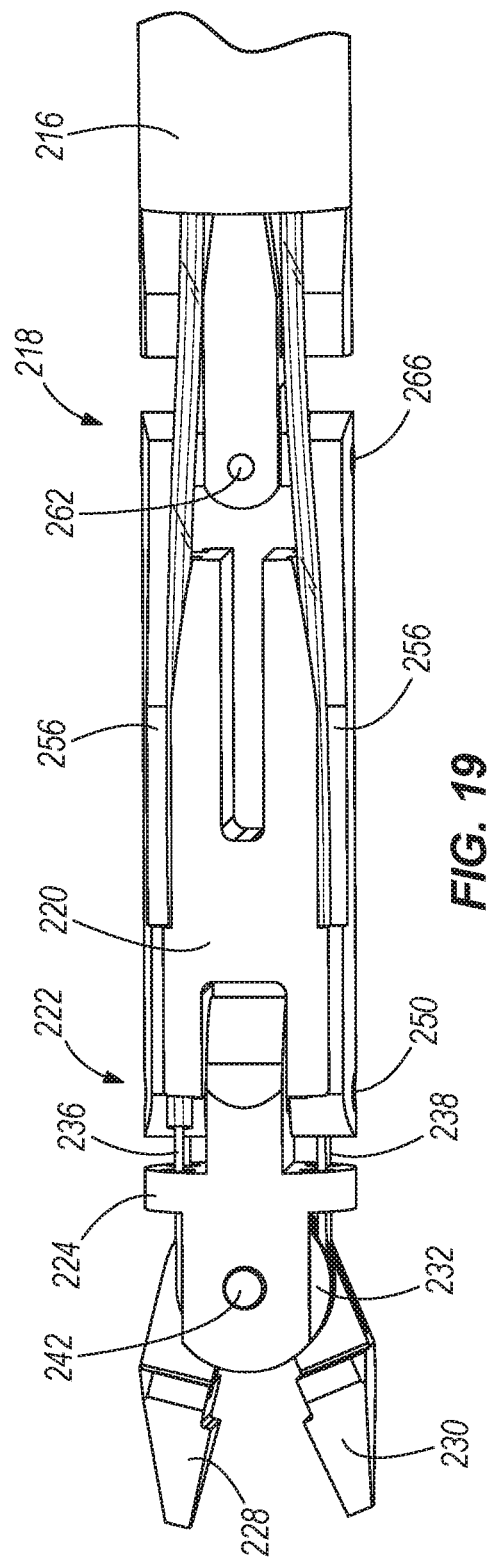
FIG. 18
FIG. 19

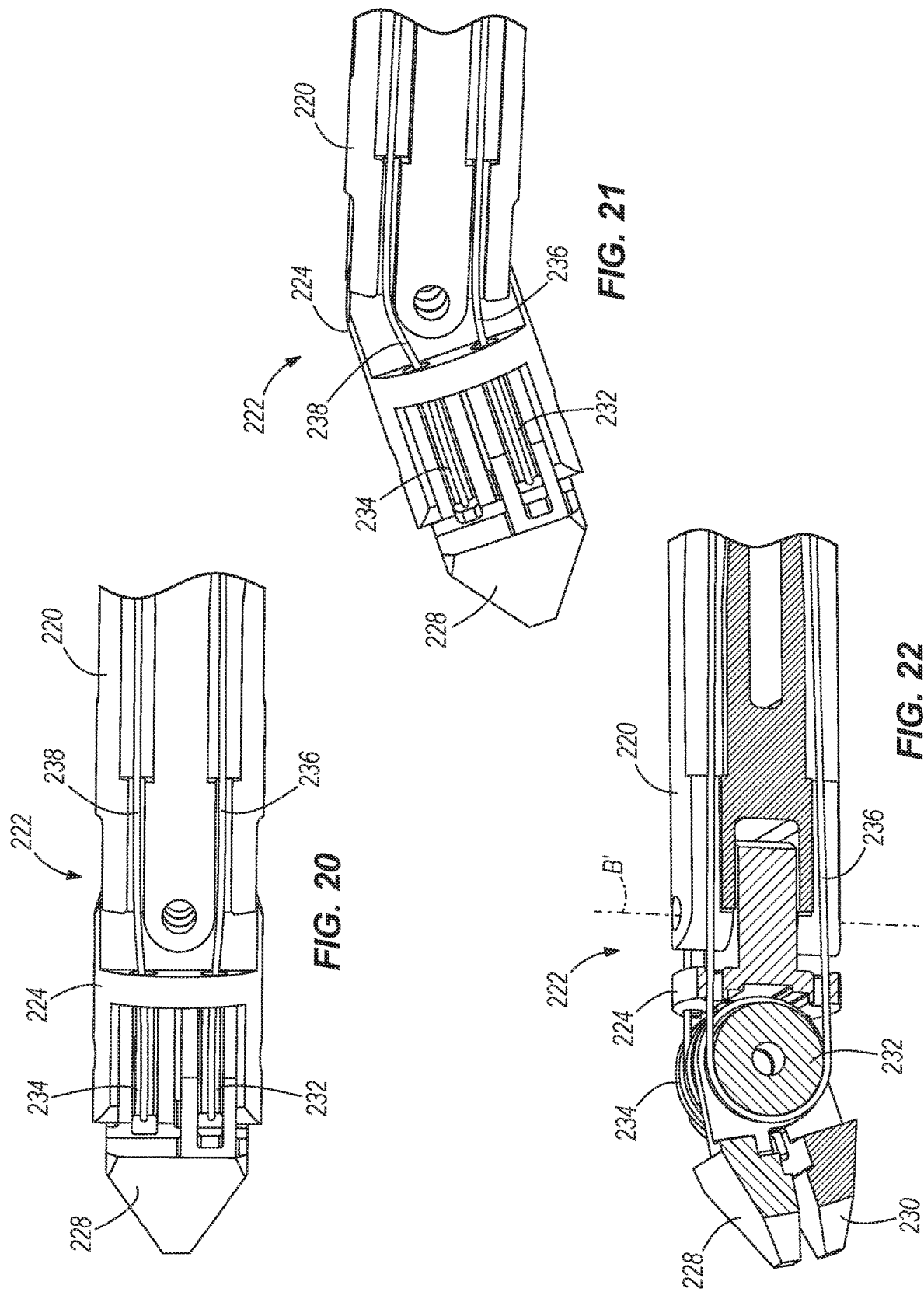

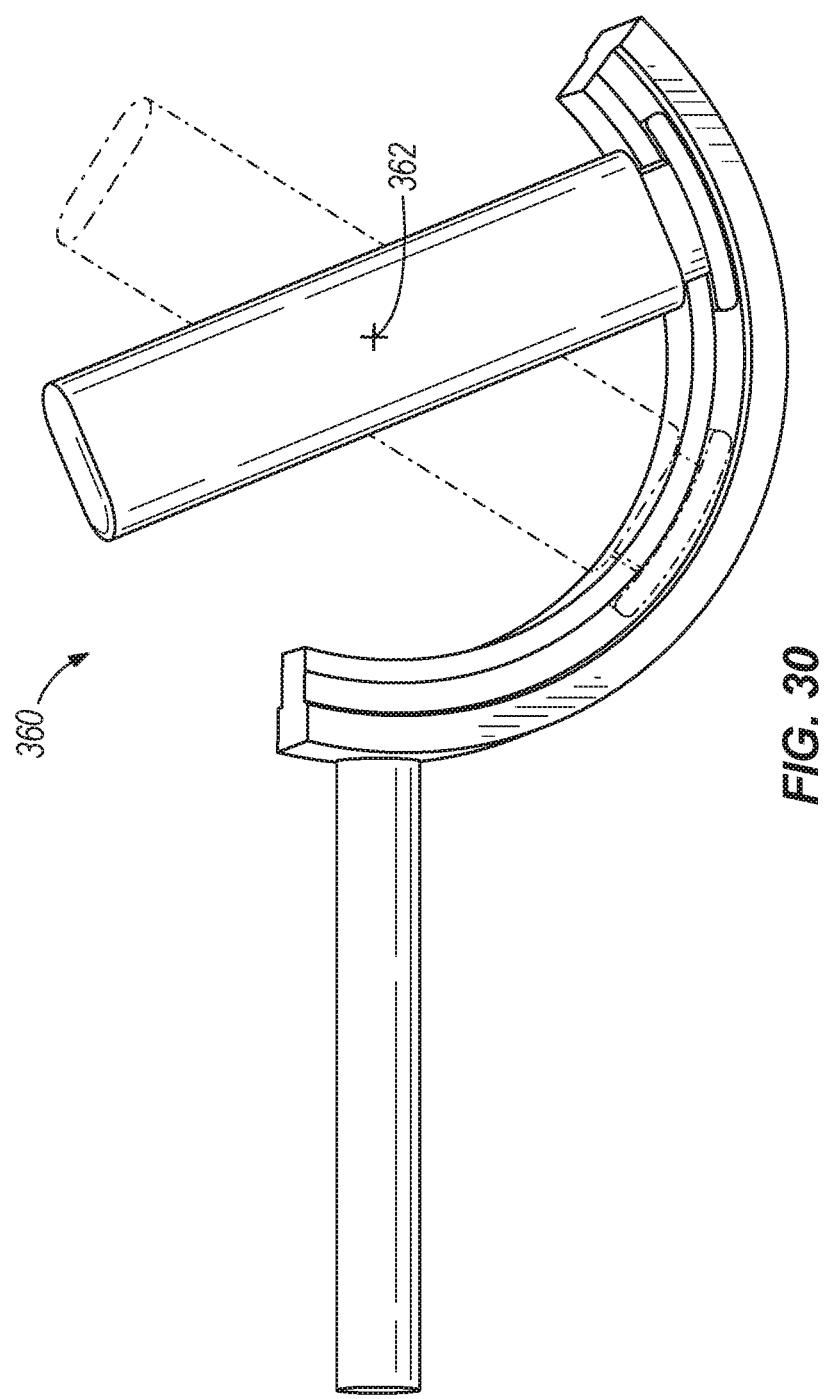

DEXTEROUS SURGICAL MANIPULATOR AND METHOD OF USE

RELATED APPLICATIONS

This application is a continuation of U.S. patent application Ser. No. 13/460,497, filed Apr. 30, 2012, and claims priority to U.S. Provisional Patent Application No. 61/481,038, filed on Apr. 29, 2011, the entire contents of each of which are incorporated herein by reference.

FIELD OF THE INVENTION

The present invention relates to a mechanical dexterous surgical manipulator for use as a tool in surgical procedures.

BACKGROUND OF THE INVENTION

Dexterous surgical manipulators provide a small surgical "hand," or gripper, which can access hard-to-reach places, such as a throat or a body cavity during laparoscopic surgery. The gripper is operable by a user interface, which translates motions performed by a surgeon on the user interface into motions performed by the gripper. User interfaces are typically non-intuitive and require practice and experience to use. Motions performed by the surgeon on the user interface may be reversed or mirrored when outputted by the gripper, and motions of the surgeon's hand may not correspond intuitively with motions of the gripper.

SUMMARY OF THE INVENTION

The surgical manipulator of the present invention provides seven degrees-of-freedom and uses an interface which maps motions of the surgeon's input to the tool's "hands." This provides the surgeon with an intuitive interface without the need for computer intervention.

In one aspect, the invention provides a surgical manipulator having an internal working end including an internal joint, and an external control interface linked to the internal working end for controlling the internal working end. The external control interface includes at least one lever defining a grip volume for a surgeon's hand when gripping and operating the at least one lever, and an external joint linked to the internal joint for controlling the internal joint. The external joint is positioned substantially within the grip volume.

In another aspect, the invention provides a surgical manipulator having a first end, and a control interface for controlling the first end. The control interface includes at least one lever being pivotable about an axis and defining a grip. The grip is positioned between the first end and the axis.

In yet another aspect, the invention provides a surgical manipulator having a first end for performing a dexterous operation, and a second end mechanically coupled to the first end for controlling operation of the first end. The first end is controlled manually by the second end. The first end includes a pair of gripper fingers each having a degree of freedom and an internal wrist joint having two degrees of freedom. The second end includes a pair of levers each having a degree of freedom for each controlling one of the pair of gripper fingers. The second end also includes an external wrist joint having two degrees of freedom for controlling the internal wrist joint. Movements of the second end are mechanically translated into movements of the first end.

The surgical manipulator of the present invention may also include the following features:

1. The size of the "hand" can be as small as 4 mm in diameter.
2. The hand can provide three degrees-of-freedom that can be controlled by a four tension wire interface. This includes both the way the hand is driven/achieves three degrees-of-freedom with only four control wires and the way the use inputs are mapped to the four control wires.
3. The use of an intuitive interface between the operating controls and the seven degrees-of-freedom of the hand provides the surgeon with an easy to learn and use interface.
4. The use of Nitnol tubes as sleeves for pull cables (similar to bicycle break cables) enables the use of very small pull cable arrangements.

The surgical manipulator offers surgeons a dexterous hand which can be used in procedures that would normally require the use of rigid laparoscopic or laparoscopic-type tool. The surgical manipulator can be suitable for use in laryngoscopic surgery or other surgical procedures, such as NOTES based operations, vaginal operations, and as a reach extension tool for working with obese patients.

BRIEF DESCRIPTION OF THE DRAWINGS

FIG. 1 is a side view of a surgical manipulator in accordance with the invention.

FIG. 2 is a simplified view of the surgical manipulator of FIG. 1.

FIG. 3 is an enlarged view of a working end of the surgical manipulator of FIG. 1.

FIG. 4 is an enlarged view of a control interface of the surgical manipulator of FIG. 1.

FIG. 5 is a side view of the working end of the surgical manipulator of FIG. 1 in a straightened position and having cables.

FIG. 6 is a cross section of the working end of the surgical manipulator of FIG. 5 taken along line 6-6.

FIG. 7 is another cross section of the working end of the surgical manipulator of FIG. 5.

FIG. 9 is an enlarged perspective view of the control interface of the surgical manipulator of FIG. 1.

FIG. 10 is a cross section of the control interface of FIG. 9 taken along line 10-10.

FIG. 11 is a cross section of the control interface of FIG. 9 taken along line 11-11.

FIG. 12 is a cross section of the control interface of FIG. 9 taken along line 12-12.

FIG. 18 is an enlarged view of a working end of the surgical manipulator of FIG. 17.

FIG. 19 is an enlarged view of the working end of the surgical manipulator of FIG. 17 in a different position.

FIG. 20 is a top view of a straight position of the working end of FIG. 17.

FIG. 21 is another top view of a bent position of the working end of FIG. 17.

FIG. 22 is a perspective and cross-section view of the working end of FIG. 18 taken through line 22-22.

FIG. 30 is an illustration of a virtual pivot.

DETAILED DESCRIPTION

Figure 8:
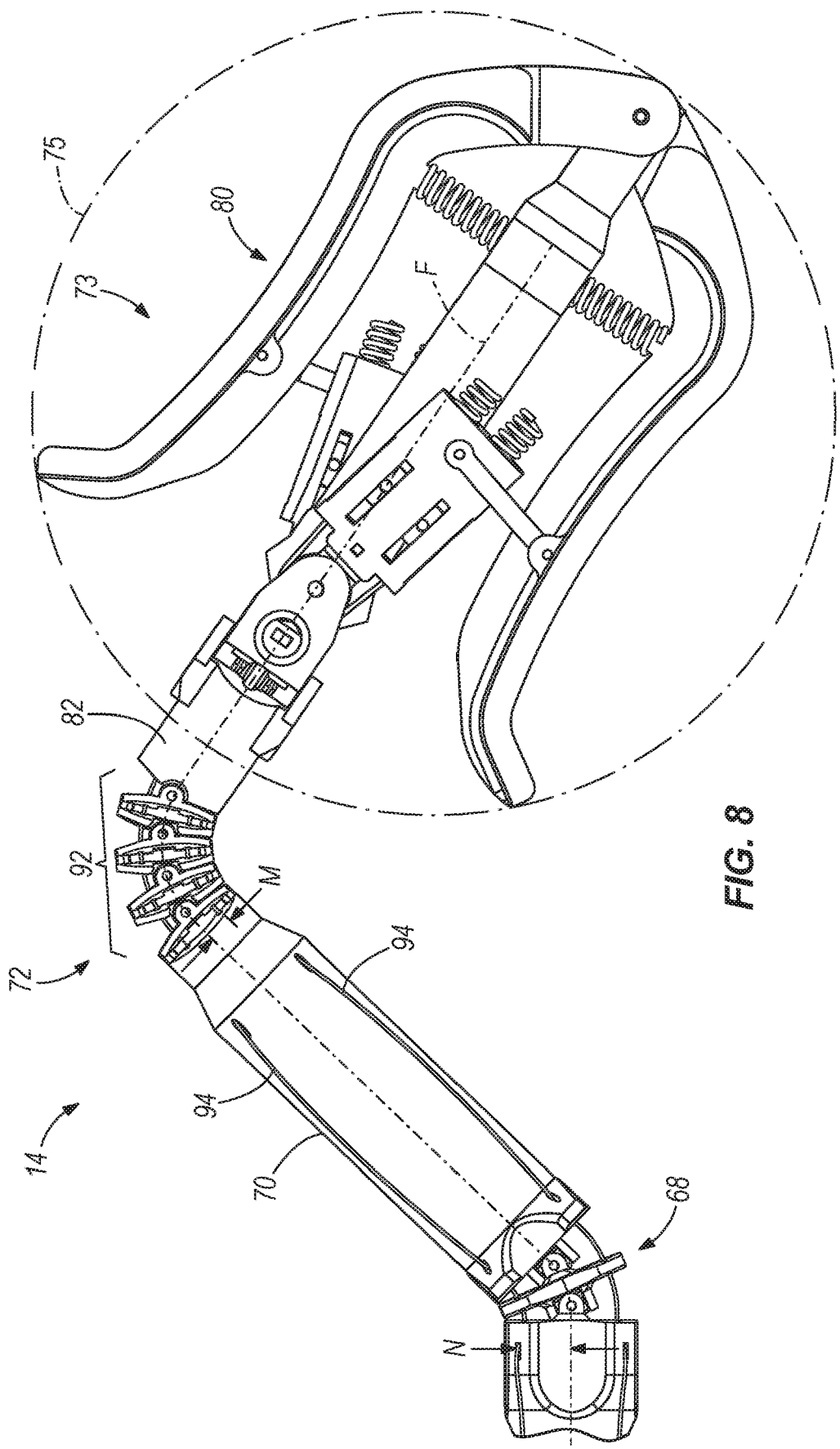
FIG. 8 is another view of the control interface of the surgical manipulator of FIG. 4 shown in a different position.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

FIG. 1 illustrates a dexterous surgical manipulator 10 according to one embodiment of the present invention. The manipulator 10 includes an internal working end 12 and an external control interface 14 connected to the internal working end 12 by a main shaft 16. "Internal" generally indicates a portion of the manipulator 10 that enters the human body through an opening while "external" generally indicates a portion of the manipulator 10 that remains outside of the human body. A center line F is defined along the surgical manipulator 10, as shown. The main shaft 16 is rigid and is formed of a suitable rigid material, such as carbon fiber or stainless steel and has a diameter of approximately 4 mm. The internal working end 12 also preferably has a diameter, measured perpendicular to the center line F, of approximately 4 mm. In other constructions, the size of the surgical manipulator 10 may be scaled as desired. Furthermore, a length of the main shaft 16 may be chosen to suit a particular application, as desired.

With particular reference to FIG. 3, the internal working end 12 includes an internal elbow joint 18 adjacent the main shaft 16, an internal forearm 20 adjacent the internal elbow joint 18, an internal wrist 24 positioned adjacent the internal forearm 20, an internal wrist joint 22 positioned between the internal forearm 20 and the internal wrist 24, and a gripper 26 positioned adjacent the internal wrist 24 including a first gripper finger 28 and a second gripper finger 30.

With particular reference to FIGS. 5-7, the first gripper finger 28 includes a first gripper pulley 32 for receiving a first drive cable 36, and the second gripper finger 30 includes a second gripper pulley 34 for receiving a second drive cable 38, as will be described in greater detail below. A pulley, as defined herein, is a generally curved or angled surface for receiving a cable thereabout to change the direction of the cable. In the illustrated construction, the pulleys 32, 34 are generally circular or semi-circular shaped surfaces having a groove therein for receiving the respective cable 36, 38 thereabout, as shown in FIG. 7. In other constructions, the pulleys described herein may have other suitable shapes and configurations.

The first gripper finger 28 includes an aperture 40a for receiving a gripper pivot pin 42, and the second gripper finger 30 includes an aperture 40b for receiving the gripper pivot pin 42. The internal wrist 24 includes a wrist pulley 44 and a pair of ears 46a, 46b. The wrist pulley 44 and ears 46a, 46b are connected by a central portion 48. The pair of ears 46a, 46b include an aperture 40c therethrough for receiving the pivot pin 42. The apertures 40a, 40b and 40c are aligned coaxially along a gripper pivot axis A defined by the gripper pivot pin 42, the apertures 40a, 40b and 40c aligning to effectively form a single aperture 40 (FIG. 7) for receiving the gripper pivot pin 42. The first and second gripper pulleys 32, 34 are centered about the gripper pivot axis A. The first and second gripper fingers 28, 30 and the internal wrist 24 are pivotably coupled by the pivot pin 42.

The wrist pulley 44 includes an aperture 52a therethrough for receiving a wrist pivot pin 50 defining a wrist pivot axis B. The wrist pulley 44 is a generally circular or semi-circular shaped surface having a groove therein for receiving a third drive cable 54 therearound, as shown in FIG. 6 and which will be described in greater detail below.

The internal forearm 20, positioned adjacent the wrist pulley 44 at a first axial end, is a generally cylindrical structure including an aperture 52b at one end receiving the wrist pivot pin 50 therethrough. The apertures 52a and 52b are aligned coaxially. The internal wrist joint 22 is generally defined by the wrist pulley 44 being pivotably connected to the internal forearm 20 by way of the wrist pivot pin 50.

The internal forearm 20 includes first cable passages 56 (FIG. 7) and second cable passages (not shown) for receiving the first and second drive cables 36, 38, respectively, and third cable passages 58 (FIG. 6) for receiving the third drive cable 54. The second cable passages are generally mirror images of the first cable passages 56 positioned on an opposite side of the internal forearm 20. The cable passages 56, 58 extend generally axially, substantially parallel with the center line F, between a first axial end adjacent the wrist pulley 40 and a second axial end adjacent the internal elbow joint 18.

With particular reference to FIG. 5, the elbow joint 18 includes first, second and third elbow pieces 60a, 60b, 60c, respectively. The first elbow piece 60a is pivotably coupled to the second axial end of the internal forearm 20 by a first elbow pivot pin 62 defining a first elbow pivot axis C1. The third elbow piece 60c is pivotably coupled to the second elbow piece 60b by a second elbow pivot pin 64 defining a second elbow pivot axis C2. The first elbow pivot pin 62 is parallel to the second elbow pivot pin 64. Likewise, the first elbow pivot axis C1 is parallel to the second elbow pivot axis C2. Pivot axes C1 and C2 cooperate to define a single degree of freedom of the internal elbow joint 18.

The first elbow piece 60a is coupled to the second elbow piece 60b by a third elbow pivot pin 66 defining a third elbow pivot axis E. The third elbow pivot pin 66 is substantially perpendicular to the first and second elbow pivot pins 62, 64. Likewise, the third elbow pivot axis E is substantially perpendicular to the first and second elbow pivot axes C1, C2. Thus, the third elbow pivot axis E defines a second degree of freedom of the internal elbow joint 18.

The elbow joint 18 also includes apertures generally axially therethrough, substantially parallel to the center line F, further defining the first, second and third cable passages 56, 58 (the second cable passages not shown) for receiving the first, second and third drive cables 36, 38, 54, respectively.

With reference to FIG. 4, the external control interface 14 includes an external elbow 68 coupled to an end of the main shaft 16 opposite the internal working end 12, an external forearm 70 coupled to the external elbow 68, a compensation mechanism 72 coupled to the external forearm 70, a stub link 82 coupled to the compensation mechanism 72, an external wrist 74 coupled to the stub link 82, an external wrist joint 76 between the stub link 82 and the external wrist 74, a user control 80 coupled to the external wrist 74 and a finger control joint 78 between the user control 80 and the external wrist 74.

The external elbow 68 includes a middle elbow disc 84 coupled to the main shaft 16 by a first external elbow pin 86 on one side and coupled to the external forearm 70 by a second external elbow pin 88 on another side opposite the first side. The first and second external elbow pins 86, 88 are substantially parallel to each other, thus defining a degree of freedom of movement of the external elbow 68. The middle elbow disc 84 is also coupled to the main shaft 16 by a third external elbow pin (not shown) that extends substantially perpendicular to the first external elbow pin 86, forming a first universal joint, and is also coupled to the external forearm 70 by a fourth external elbow pin (not shown) that is substantially perpendicular to the second external elbow pin 88, forming a second universal joint. Thus, the external elbow 68 has a first degree of freedom defined by the first and second external elbow pins 86, 88 (i.e., the first universal joint) and a second degree of freedom defined by the third and fourth external elbow pins (i.e., the second universal joint). The external elbow 68 includes apertures 90 extending generally axially, substantially parallel with the center line F, further defining the first, second and third cable passages 56, 58. The external forearm 70 also includes apertures (not shown) extending generally axially, substantially parallel with the center line F, further defining the first, second and third cable passages 56, 58. The third cable passage 58 and the third drive cable 54 are twisted 180 degrees inside the external forearm 70.

The compensation mechanism 72 is best illustrated in FIG. 8 and includes a secondary joint 92 positioned between the stub link 82 and the external forearm 70 and a cable 94 connecting the stub link 82 to the external elbow 68 via the secondary joint 92, as shown. The cable 94 is mounted a first distance M from the centerline F proximate the secondary joint 92, and is mounted a second distance N from the centerline F proximate the external elbow 68. The second distance N is twice the first distance M. In the illustrated construction, a change in angle of the external elbow 68 causes twice the change in angle of the secondary joint 92. For example, when the external elbow 68 is flexed 10 degrees, the secondary joint flexes twice as much, i.e., 20 degrees. Thus, the secondary joint 92 and the external elbow 68 are linked by the cable 94. That is, movement of the external elbow 68 causes movement of the secondary joint 92. More specifically, movement of the external elbow 68 causes twice the movement in the secondary joint 92. In other constructions, other distances may be employed. For example, the second distance may be one and a half times the first distance, or three times the first distance, etc. This relationship achieves a desired compensation by choosing a ratio of relative movement such that a movement of the external elbow 68 causes a larger movement of the secondary joint 92. The purpose of the compensation mechanism will be explained in further detail below.

The stub link 82 is coupled to the compensation mechanism 72 at one end and at an opposite end includes an aperture 96 for receiving an external wrist pin 98 defining an external wrist pivot axis G. The external wrist 74 includes an aperture 100 receiving the external wrist pin 98, thus pivotably coupling the stub link 82 to the external wrist 74. The aperture 96 is aligned coaxially with the aperture 100. The external wrist joint 76 is generally defined by the stub link 82 including the aperture 96, the external wrist 74 including the aperture 100 and the external wrist pin 98 passing through the apertures 96, 100.

The external wrist 74 includes a pulley 102 and a termination area 104 in which the third drive cable 54 is terminated. In the illustrated construction, the pulley 102 receives the drive cable 54 and two free ends of the drive cable 54 are secured and fixed to the termination area 104 of the external wrist 74.

The external wrist 74 is pivotably coupled to the stub link 82 at one end and at an opposite end includes an aperture 106 for receiving an external gripper pin 108 defining an external gripper axis H.

The external control interface 14 includes a user control 80. The user control 80 includes first and second gripper levers 110, 112, respectively. The first and second gripper levers 110, 112 are pivotably coupled to each other and to a support member 114 by a lever pin 116 defining a lever axis J. Each of the first and second gripper levers 110, 112 are independently pivotable with respect to the support member 114 and are biased away from the support member 114 to an open position by respective springs 111, 113 disposed between the first and second gripper levers 110, 112 and the support member 114, respectively. The support member 114 is coupled to the gripper levers 110, 112 at a first end and is coupled to the external wrist by way of the external wrist pin 98 at a second end opposite the first end. The first gripper lever 110 is pivotably connected to a first link 118, which is in turn pivotably connected to a first cable box 120, which is in turn pivotably connected to the external wrist 74 by way of the external wrist pin 98. Likewise, the second gripper lever 112 is pivotably connected to a second link 122, which is in turn pivotably connected to a second cable box 124, which is in turn pivotably connected to the external wrist 74 by way of the external wrist pin 98. Thus, the first and second cable boxes 120, 124 are pivotable about the external wrist pin 98 independently of each other.

Furthermore, the first and second cables 36, 38 are routed around the wrist joint (FIG. 12). Changes in length of the cables 36, 38 in the area proximate the external wrist pin 98 are a result of articulation of the wrist joint 76. They are mirrored by similar changes at the gripper end of the device, as will be explained in greater detail below. Thus, the position of the gripper fingers 28, 30 should be unaffected by articulation of the external wrist joint 76.

As best shown in FIG. 10, the first cable box 120 and the second cable box 124 (not shown in FIG. 10) include a pulley 126 and a termination area 128. The first and second cable boxes 120, 124 also include optional first and second spring cavities 130, 132 extending parallel to each other and receiving first and second springs 134, 136, respectively. The second cable box 124 is substantially the same as the first cable box 120 and is therefore not illustrated in cross-section, although a pulley 138 of the second cable box 124 can be seen in the cross section of FIG. 12.

With further reference to FIG. 10, the pulley 126 receives the first drive cable 36 thereabout. The first drive cable 36 includes two free ends, each of which is secured and fixed in the termination area 128 of the first cable box 120. The free ends of the drive cable 36 are optionally coupled to the first and second springs 134, 136, respectively, for maintaining a level of tension on the drive cable 36. Likewise, the pulley 138 (FIG. 12) in the second cable box 124 receives the second drive cable 38 thereabout. The second drive cable 38 includes two free ends, each of which is secured and fixed in the termination area (not shown) of the second cable box 124 and may optionally be secured to springs, as described above.

Figure 13:
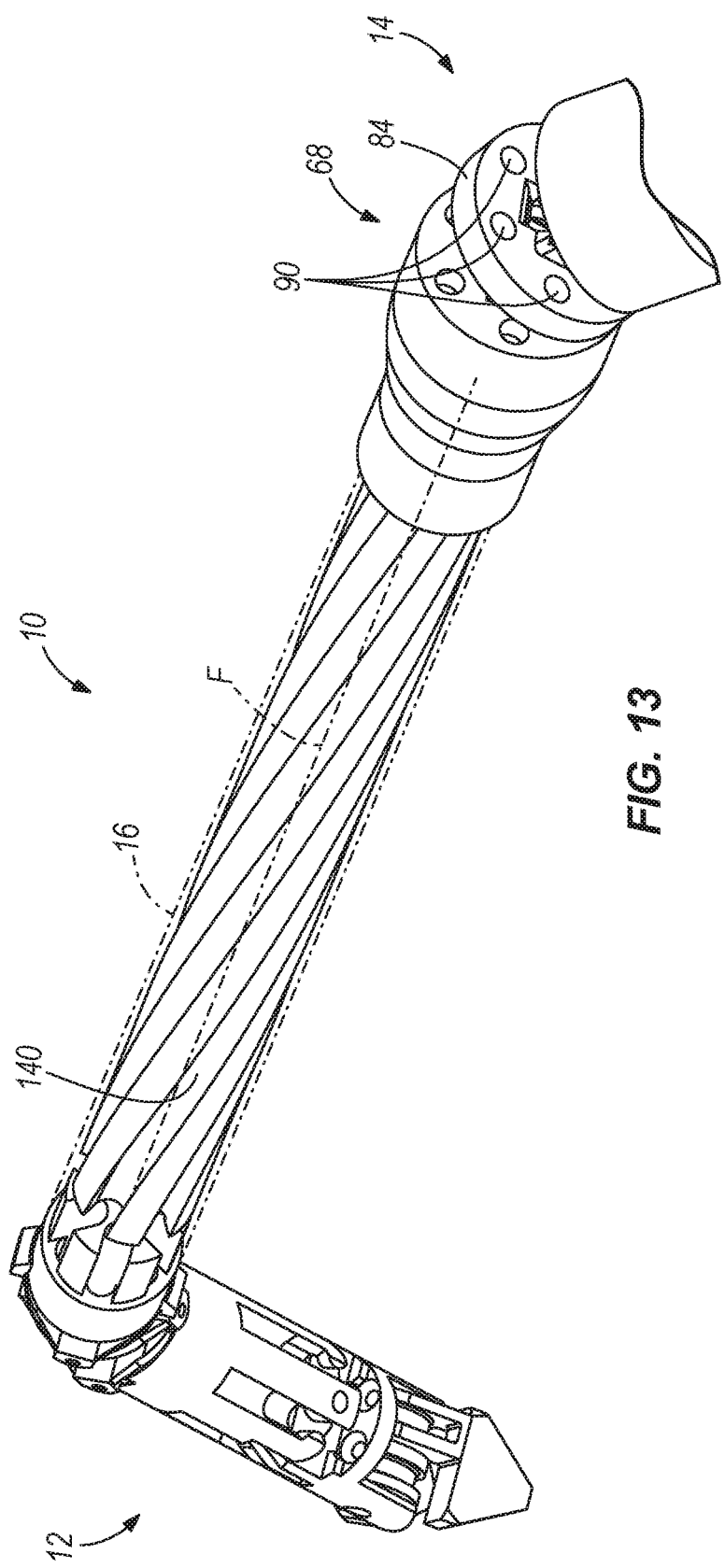
FIG. 13 is a rear perspective view of a portion of the surgical manipulator of FIG. 1.

FIG. 13 illustrates the surgical manipulator 10 having a transparent main shaft 16 for illustration purposes. Inside the main shaft 16 is a core spacer 140 which carries the first, second and third drive cables 36, 38, 54 from the internal elbow 18 to the external elbow 68. The core spacer 140 includes a twist of 180 degrees with respect to the centerline F, which causes each of the drive cables 36, 38, 54 to twist 180 degrees with respect to the centerline F between the internal elbow 18 to the external elbow 68. For example, a cable that passes through the internal elbow 18 at the top of the joint will pass through the external elbow 68 at the bottom of the joint.

Each cable 36, 38, 54 is received inside a respective sleeve pair 142, 144, 146 (FIG. 5) extending from the internal elbow 18 through the main shaft 16 to the external elbow 68. The sleeves 142, 144, 146 may be made of nickel titanium, or another suitable material. Each cable 36, 38, 54 originates at the external control interface end 14, loops around a pulley at the internal working end 12, and returns to the external control interface end 14, thus necessitating a pair of sleeves for each cable 36, 38, 54, one for a portion of the cable on one side of the respective pulley and one for a portion of the cable on the other side of the respective pulley. Each sleeve 142, 144, 146 is secured at a first end to the internal forearm 20, as shown in FIG. 5, and secured at a second end to the external forearm 70. Thus, the sleeves 142, 144, 146 provide a path for the cables 36, 38, 54 to follow that has a constant length, regardless of the orientation of the internal and external elbow joints 18, 68, such that actuation of the cables 36, 38, 54 for driving the first and second gripper fingers 28, 30 and the internal wrist joint 22 is independent from actuation of the internal elbow joint 18.

Furthermore, the sleeves 142, 144, 146 themselves act as drive cables to actuate the internal elbow joint 16 in response to movement of the external elbow 68. This provides dual functionality for the sleeves 142, 144, 146: carrying the cables 36, 38, 54 and operably connecting the internal and external elbows 18, 68. The sleeves 142, 144, 146 are twisted 180 degrees with respect to the center line F by the core spacer 140.

FIG. 2 schematically illustrates the angular relationship between linkages of the surgical manipulator 10. An external gripper angle A1 is defined between the user control 80 and the external forearm 70. An external elbow angle A2 is defined between the external forearm 70 and the main shaft 16. An internal elbow angle A3 is defined between the main shaft 16 and the internal forearm 20. An internal gripper angle A4 is defined between the internal forearm 20 and the gripper 26. The design intent is to keep the user control 80 and the gripper 16 parallel. In order to keep the user control 80 and the gripper 16 parallel, the following equation must be satisfied: $A4=A1-(A3+A2)$. It is known, by design, that the internal and external elbow angles A3 and A2 are equal in magnitude. Therefore, in order to keep the user control 80 and the gripper 16 parallel, the mechanics of the surgical manipulator 10, 150 must be such that the gripper angle A4 depends upon, i.e., is controlled by, both the external gripper angle A1 and the and the external elbow angle A2. In other words, the mechanics of the surgical manipulator 10 must be such that the external gripper angle A1 and the external elbow angle A2 are linked or connected in such a way that ensures that the equation is satisfied. The compensation mechanism 72 provides the needed relationship.

Figure 29:
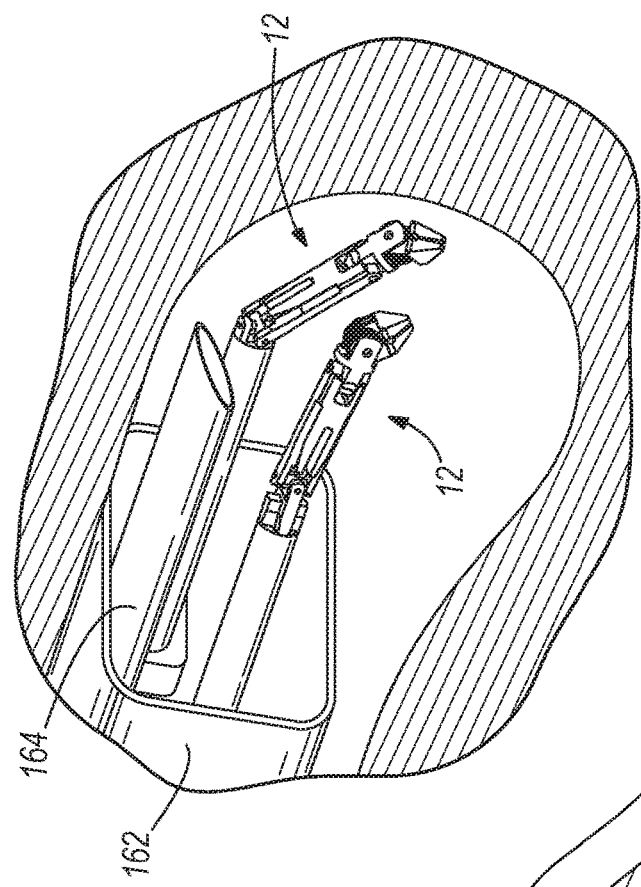
FIG. 29 is an enlarged view of two surgical manipulators in use for throat surgery.
Figure 28:
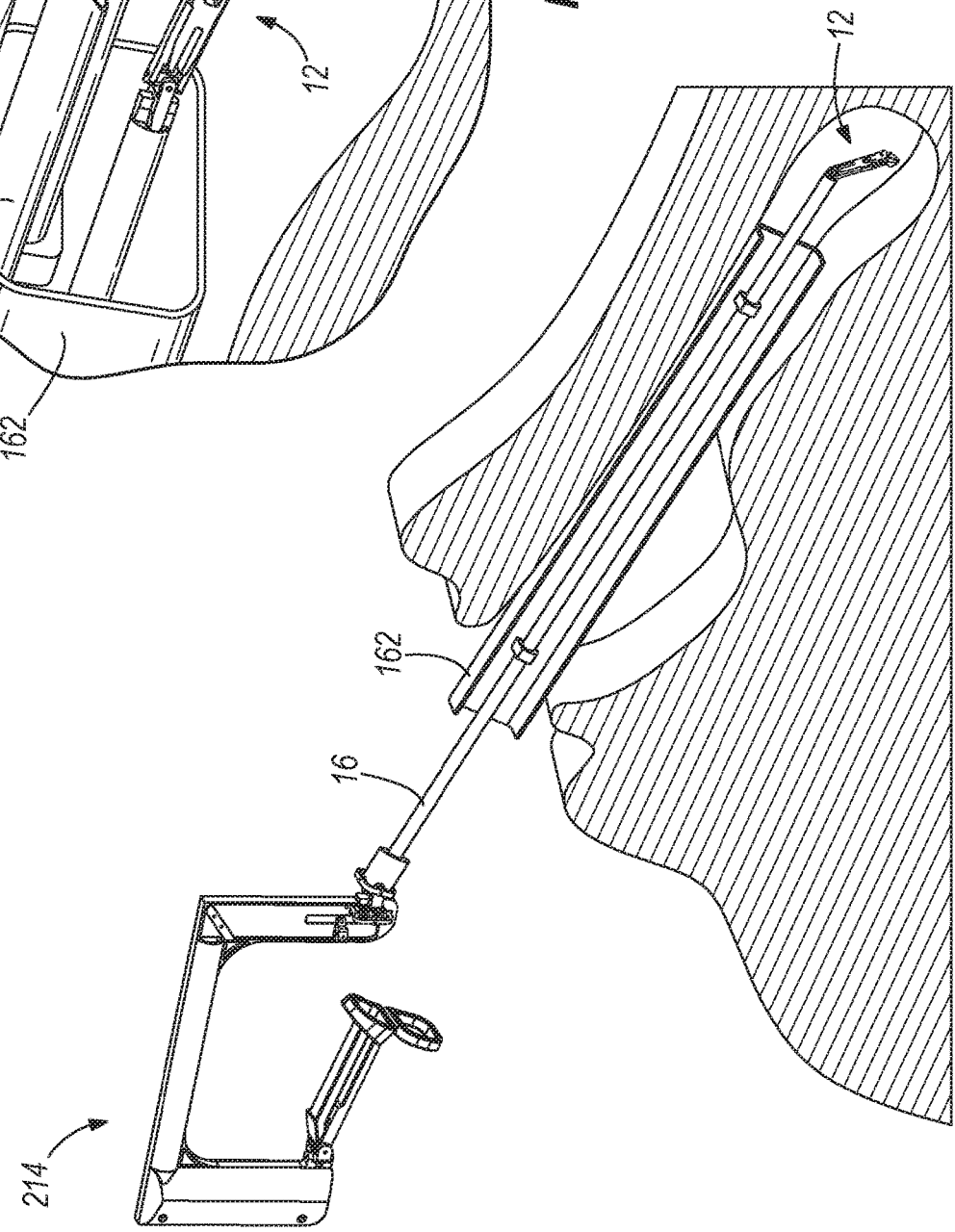
FIG. 28 is a perspective view of the surgical manipulator of FIG. 17 in use for throat surgery.

In operation, the surgical manipulator 10 is used by a surgeon as a tool during surgery. The shaft 16 of the surgical manipulator 10 can be placed to pass from outside of a patient's body to the inside of a patient's body such that the internal working end 12 is positioned inside the patient's body. For example, as shown in FIGS. 28-29, a laryngoscope 162 is placed in a patient's mouth/throat and the shaft 16 is mounted in the laryngoscope 162. An endoscope 164 (FIG. 29) may also be passed through the laryngoscope 162. The surgeon manipulates the external control interface (shown as a different construction) in order to manipulate the position of the gripper 26 at the end of the internal working end 12 in order to perform a desired operation, such as gripping a needle or performing a stitch. The surgical manipulator 10 may similarly be used in laparoscopic surgery.

The first gripper finger 28 is individually controlled by the first gripper lever 110 and the second gripper finger 30 is individually and independently controlled by the second gripper lever 112. The first drive cable 36 is coupled between the first cable box 120 and the first pulley 32. When the first gripper lever 110 is squeezed towards the support member 114, the first cable box 120 pivots about the external gripper axis H. As both free ends of the first drive cable 36 are terminated and fixed to the first cable box 120 (FIG. 10), when the first cable box 120 pivots about the external gripper axis H, the first cable box 120 pulls one free end of the first drive cable 36 and feeds the other free end of the first drive cable 36 within the surgical manipulator 10. This causes the first pulley 32 to rotate about the gripper pivot axis A, causing rotation of the entire first gripper finger 28 about the pivot axis A.

For example, when the surgeon squeezes the first gripper lever 110 towards the support member 114, the first cable box 120 pivots towards the support member 114, which pulls a free end 36a of the first cable 36 shown in light red (top) and feeds a free end of the cable 36b shown in dark red (bottom). Since the cable 36 is twisted 180 degrees inside the main shaft 16, the top portion of the cable 36 about the pulley 32 (FIG. 7) is given slack and the bottom portion of the cable 36 is pulled, thus rotating the first gripper finger 28 towards the second gripper finger 30 towards a closed position. The same description applies to the movement of the second gripper finger 30. Thus, squeezing the first and second gripper levers 110, 112 towards each other, i.e., towards the support member 14, causes the gripper 26 to close. This mapping of motion is intuitive to the user.

Furthermore, the lever pivot axis J is positioned at the back of the external control interface 14, behind the first and second gripper levers 110, 112. In other words, the first and second gripper levers 110, 112 are located between the lever pivot axis J and the internal working end 12 in the direction of the center line F. Furthermore, the first and second gripper levers 110, 112 are substantially symmetric about the center line F, both vertically symmetric and left-and-right symmetric. This provides an ambidextrous user control 80.

The internal elbow joint 18 is controlled by the external elbow joint 68. To control the internal elbow joint 18, the surgeon flexes the external elbow 68. The internal elbow joint 18 and the external elbow 68 are coupled to each other by the sleeve pairs 142, 144, 146. The sleeve pairs 142, 144, 146 twist 180 degrees inside the main shaft 16 with respect to the center line F. Therefore, when the surgeon flexes the external elbow 68 down, as shown in FIGS. 1-2, such that the external forearm 70 forms the angle A2 with the main shaft 16, the internal elbow joint A3 also flexes down such that the internal forearm 20 forms the angle A3 with the main shaft 16, the angles A2 and A3 being substantially equal.

The secondary joint 92 is constrained by the compensation mechanism 72 to flex twice as much as the external elbow 68. Therefore, when the surgeon flexes the external elbow 68, the compensation mechanism 72 also flexes. The internal gripper angle A4 is thus controlled by both the external elbow angle A2 and the external gripper angle A1 such that the gripper 26 remains substantially parallel to the user control 80.

As the sleeve pairs 142, 144, 146 are coupled between the internal and external forearms 20, 70 and span the entire length of both the internal and external elbow joints 18, 68, the path length of the cables 36, 38 54 is not changed by flexing of the internal and external elbow joints 18, 68. Therefore, elbow joint control is independent from all other control of the internal working end 12 with one exception: because the compensation mechanism 72 links movement of the external elbow 68 with movement of the secondary joint 92 and thus with the angle A1 of the user control 80, the angle A4 of the gripper 26 is dependent, albeit not directly, on the angle A2 of the external elbow 68 as well as the angle A1 of the user control 80. Thus, the compensation mechanism 72 helps the surgical manipulator 10 satisfy the equation to keep the gripper 26 substantially parallel to the user control 80. This mapping is intuitive for the user.

The internal wrist joint 22 is controlled by the external wrist 74 pivoting about the external wrist pivot axis G. The third drive cable 54 is coupled between the wrist pulley 44 (FIG. 6) and the external wrist pulley 102 (FIG. 11). Since the third cable 54 is twisted 180 degrees inside the main shaft 16 and subsequently untwisted inside the external forearm 70, the external wrist 74 and internal wrist 24 move in a parallel manner. That is, when the external wrist 74 is pivoted counterclockwise about the external wrist pivot axis G, the internal wrist 24 is also pivoted counterclockwise about the wrist pivot axis B such that the internal wrist 24 is substantially parallel with the external wrist 74. As both free ends of the third drive cable 54 are terminated and fixed to the external wrist 74 (FIG. 11), when the external wrist 74 pivots about the external wrist pivot axis G, the external wrist 74 pulls one free end of the third drive cable 54 and feeds the other free end of the third drive cable 54 within the external wrist 74. This causes the wrist pulley 44 to rotate about the wrist pivot axis B, causing rotation of the internal wrist 24 and the gripper 26 about the wrist pivot axis B.

For example, when the surgeon pivots the user control 80 and the external wrist 74 about the wrist pivot axis G in a clockwise direction as viewed from the top (or counterclockwise direction as viewed from the bottom, e.g., FIG. 6), a free end 54a of the third cable 54 shown in dark red is pulled and a free end of the cable 54 shown in light red is fed. Therefore, a portion of the cable 54 on one side the pulley 102 (FIG. 11) is given slack and the other portion of the cable 54 is pulled, rotating the wrist pulley 44. This mapping of motion is intuitive to the user.

Furthermore, the wrist pivot axis G (and the external wrist joint 76) is positioned within the user control 80 and is therefore positioned inside a grip volume 73 of a surgeon's hand (FIG. 8) when gripping and operating the user control 80. For example, the surgeon's hand may grip the first and second gripper levers 110, 112. In some constructions, the surgeon's hand may grip a first pivotable lever (e.g., the first gripper lever 110 or the second gripper lever 112) and a second stationary lever (e.g., the other of the first gripper lever 110 and the second gripper lever 112 being configured as non-pivotable), the first pivotable lever pivoting with respect to the second stationary lever. As illustrated in FIG. 8, the external wrist joint 76 can also be defined as being located within a spherical grip volume 75 including the first and second gripper levers 110, 112. As can be seen in FIGS. 4 and 9-11, the wrist pivot axis G intersects the user control 80, and more specifically intersects at least the first gripper lever 110. Positioning the wrist pivot axis G within the grasp of an operator provides intuitive mapping of motion. In other constructions, a sliding mechanism having a virtual pivot 360 could be used, as illustrated in FIG. 30. The virtual pivot point 362 would also lie within the grip of a user's hand.

As shown in FIG. 12, when the wrist joint 24 at axis G is manipulated, the length of the first and second cables 36, 38 (gripper control cables) changes in the area indicated by numeral 166; however, an equal and opposite change in length occurs in each of the gripper control cables 36, 38 at the internal working end 12 of the manipulator 10 because the wrists 24, 74 are parallel. Therefore, articulation of the wrist joint 24 at axis G does not affect the position of the gripper fingers 28, 30 with respect to each other.

Thus, the internal working end 12 of the surgical manipulator 10 has seven degrees of freedom. As illustrated in FIG. 1, a first degree of freedom D1 is a sliding motion of the entire dexterous manipulator 10 in a direction parallel with the main shaft 16 caused by the surgeon pushing or pulling the dexterous manipulator 10 in said direction. A second degree of freedom D2 is a rotational motion of the entire dexterous manipulator 10 caused by the surgeon rotating the dexterous manipulator 10 about the centerline F of the main shaft 16. A third degree of freedom D3 is the pivoting of the internal elbow joint 18 about the elbow pivot axes C1 and C2 caused by the surgeon pivoting the external elbow 68 about a parallel axis. A fourth degree of freedom D4 is the pivoting of the internal elbow joint 18 about the third elbow pivot axis E, which is substantially perpendicular to the elbow pivot axes C1 and C2, caused by the surgeon pivoting the external elbow 68 about an axis substantially parallel with the third elbow pivot axis E. A fifth degree of freedom is the pivoting of the wrist about the wrist pivot axis B, which is caused by the surgeon pivoting the external wrist 74 about the external wrist pivot axis G. A sixth degree of freedom is the pivoting of the first gripper finger 28 about the gripper pivot axis A, and a seventh degree of freedom is the pivoting of the second gripper finger 30 about the gripper pivot axis A. As each gripper finger 28, 30 is controlled independently by a respective gripper lever 110, 112, each has its own degree of freedom.

Figure 14:
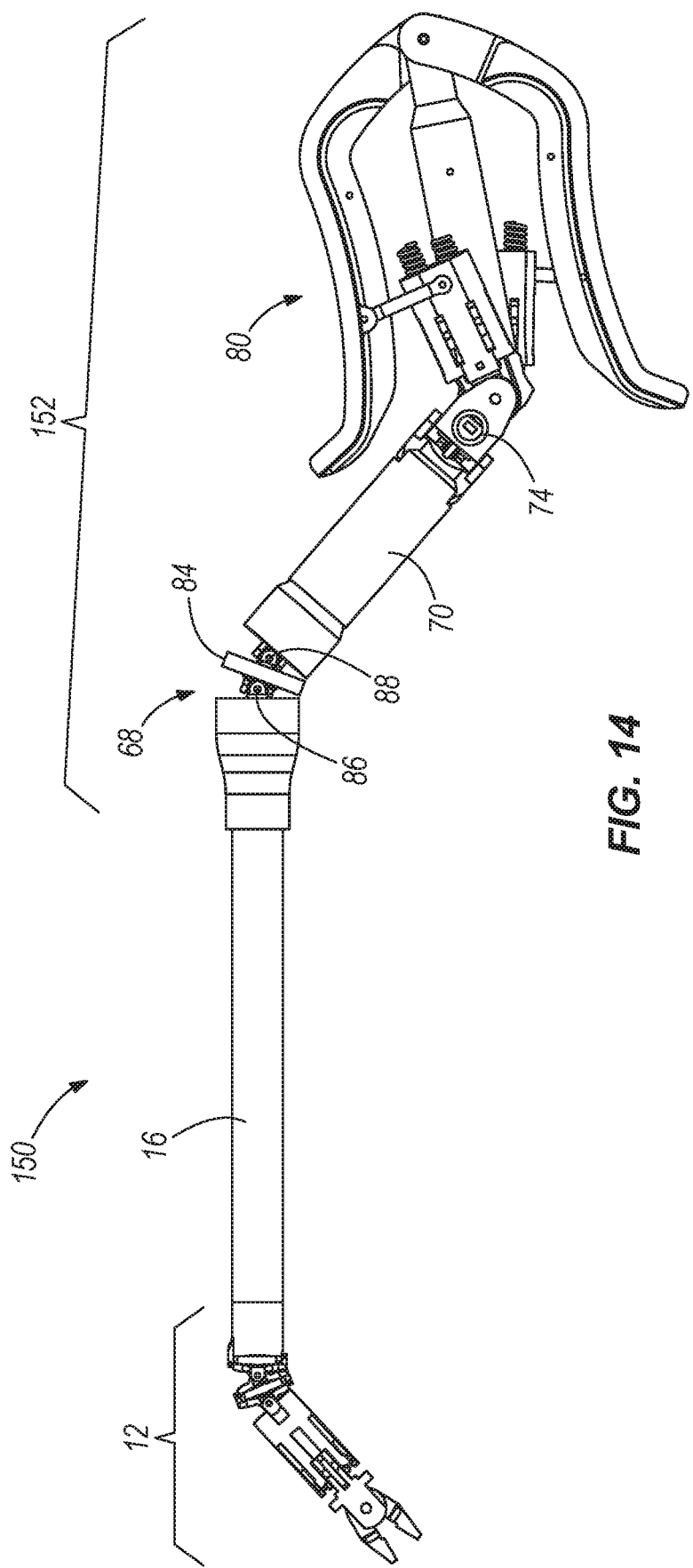
FIG. 14 is a side view of a second construction of a surgical manipulator in accordance with the invention.
Figure 15:
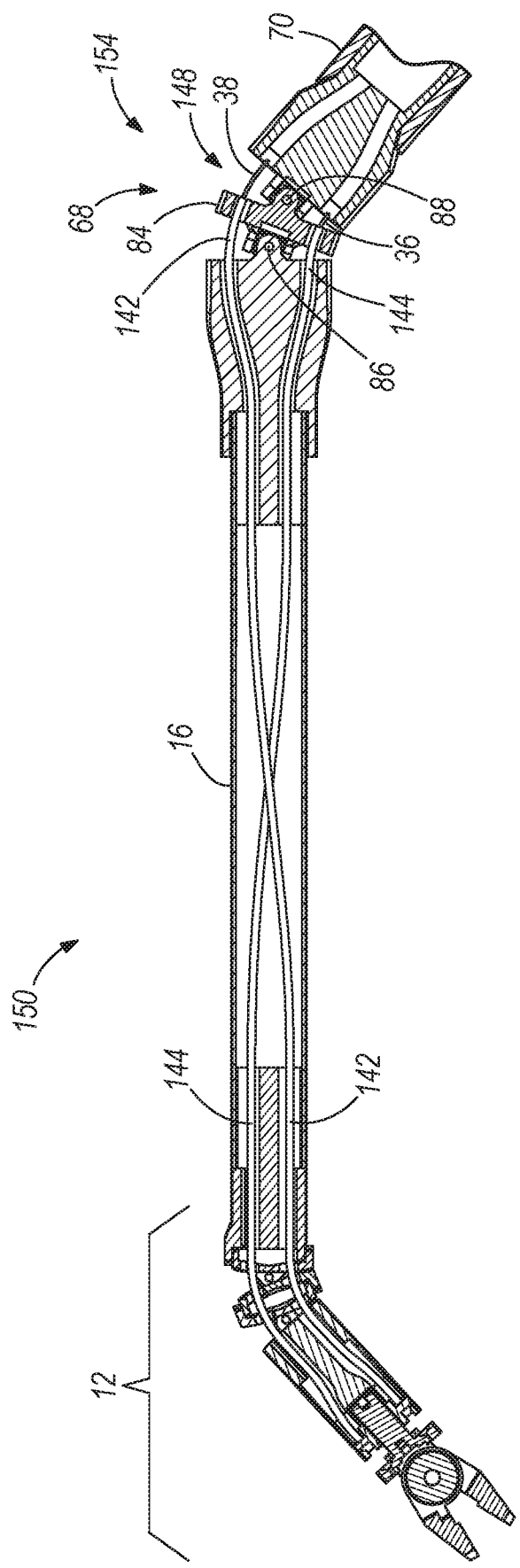
FIG. 15 is a cross section view of a portion of the surgical manipulator of FIG. 14.

FIGS. 14-15 illustrate an alternate construction of a dexterous surgical manipulator 150. The surgical manipulator 150 includes the same internal working end 12 and main shaft 16 as described above with respect to FIGS. 1-13. The surgical manipulator 150 includes an external control interface 152 that differs from the external control interface 14 described above with respect to FIGS. 1-13 in that the compensation mechanism 72, including the secondary joint 92 and the cable 94, and the stub link 82 have been eliminated. As such, the external wrist 74 is pivotably coupled to the external forearm 70. The remaining elements of the dexterous surgical manipulator 150 are substantially the same as those described above with respect to FIGS. 1-13 and need not be described again.

FIG. 15 illustrates a compensation mechanism 154 for the surgical manipulator 150. The compensation mechanism 154 provides the needed relationship between the internal gripper angle A4, the external gripper angle A1 and the external elbow angle A2, described above. The compensation mechanism 154 is embodied by the sleeves 142, 144, 146 being terminated and secured in the middle elbow disc 84, leaving the cables 36, 38, 54 exposed in a space 148 between the middle elbow disc 84 and the external forearm 70. Thus, the space between the middle elbow disc 84 and external forearm 70 changes with changes in the angle of the external elbow joint 68. As the cables 36, 38, 54 are not housed in sleeves within the space 148, the cable path length changes as the angle of the external elbow joint 68 changes. Therefore, the movement of the gripper 26 is at least partially dependent on the angle of the external elbow joint 68, as needed to satisfy the equation described above.

In operation, the surgical manipulator 150 works similarly to the surgical manipulator 10, described above, and the similar functions will not be described again. The surgical manipulator 150 functions differently from the surgical manipulator 10 in that the external elbow 68 is constructed such that the sleeve pairs 142, 144, 146 do not span the entire length of the external elbow joint 68. Rather, the sleeve pairs 142, 144, 146 terminate at the middle elbow disc 84. As a result, the path lengths of the cables 36, 38, 54 are elongated when the external elbow 68 is flexed and shortened when the external elbow 68 is unflexed. Therefore, the position of the gripper 26 (the gripper angle A4) is affected when the external elbow 68 is flexed. Thus, the internal gripper angle A4 is dependent on the position of the external elbow 68 (external elbow angle A2) and on the angle A1 of the user control 80. Thus, the compensation mechanism 154 helps the surgical manipulator 150 satisfy the equation, described above, to keep the gripper 26 substantially parallel to the user control 80. This mapping is intuitive for the user.

The gripper control for the gripper 26 of the surgical manipulator 150 is identical to the control described above with respect to the surgical manipulator 10. The wrist control for the internal wrist 24 of the surgical manipulator 150 is identical to the control described above with respect to the surgical manipulator 10.

Figure 16:
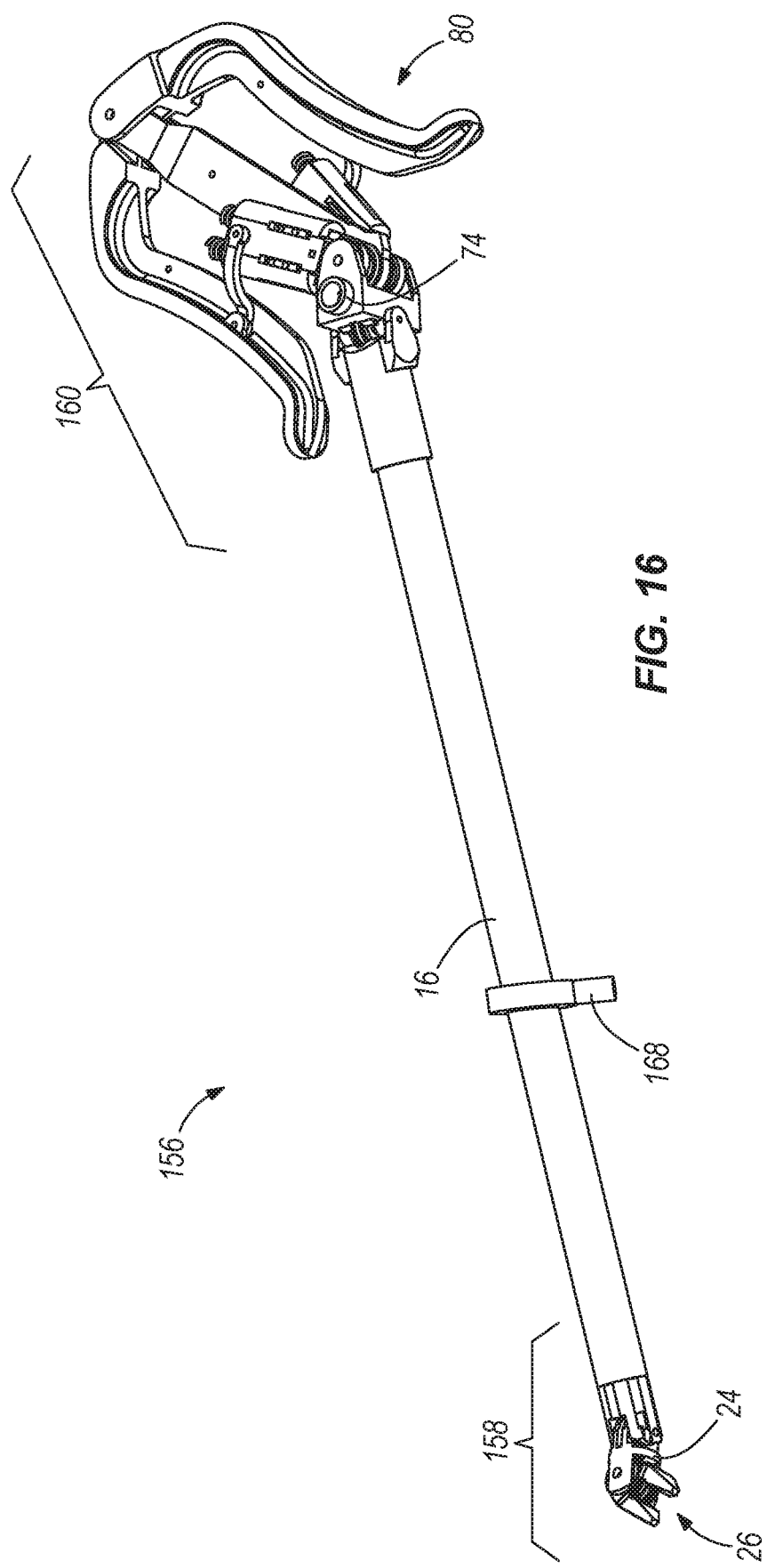
FIG. 16 is a side perspective view of a third construction of a surgical manipulator in accordance with the invention.
Figure 17:
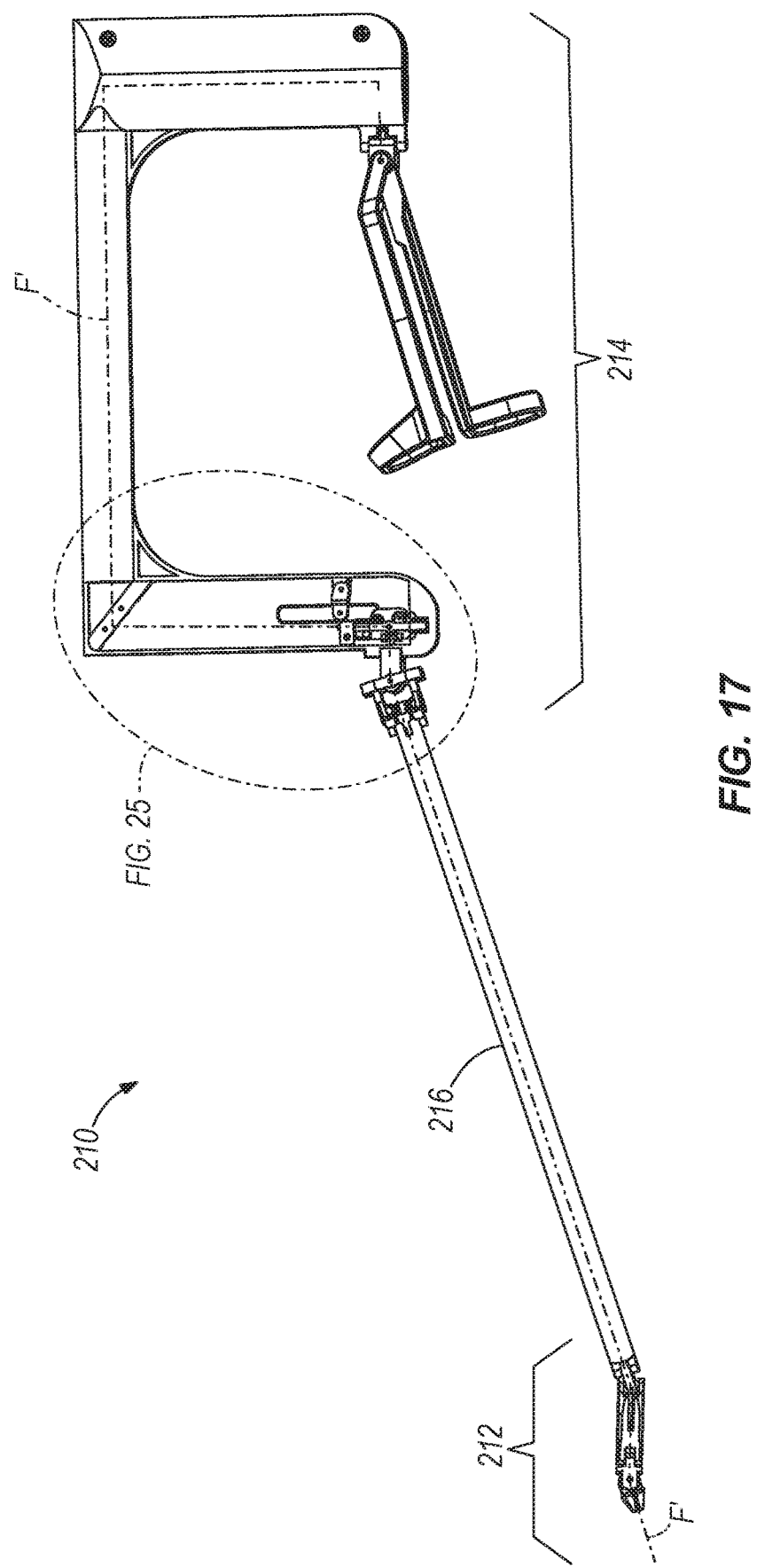
FIG. 17 is a side view of a fourth construction of a surgical manipulator in accordance with the invention.
Figure 23:
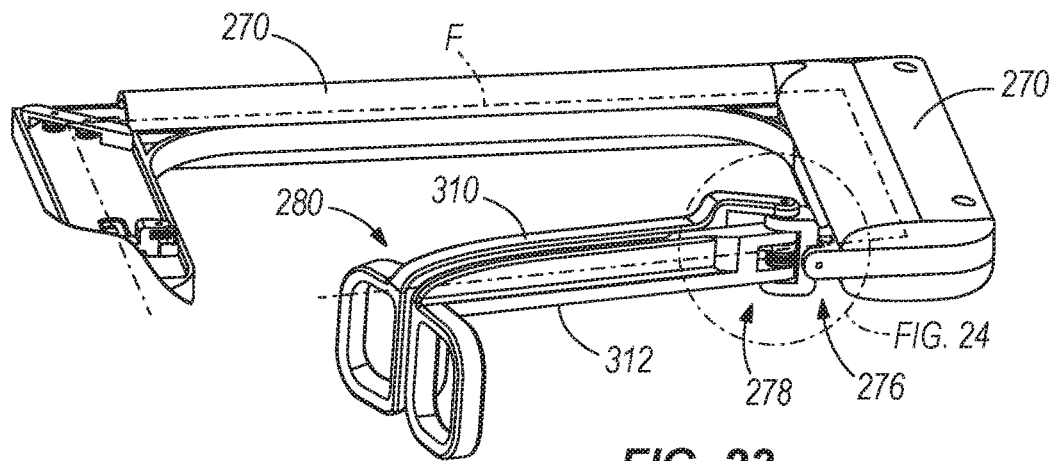
FIG. 23 is a perspective view of a portion of a control interface of the surgical manipulator of FIG. 17.

FIG. 16 illustrates yet another alternate construction of a dexterous surgical manipulator 156. The surgical manipulator 156 includes the same main shaft 16 as described above with respect to FIGS. 1-13 and includes an internal working end 158 and an external control interface 160. The internal working end 158 is substantially the same as the construction described above with respect to FIGS. 1-13 except that the internal forearm 20 and the internal elbow joint 18 are eliminated. As such, the internal wrist 24 is pivotably coupled to the main shaft 16. The external control interface 160 is substantially the same as the construction described above with respect to FIGS. 1-13 except that the external elbow, external forearm 70, compensation mechanism 72 and stub link 82 have been eliminated. As such, the external wrist 74 is pivotably coupled to the main shaft 16. Remaining elements of the dexterous surgical manipulator 156 are substantially the same as those described above with respect to FIGS. 1-13 and need not be described again.

In operation, the surgical manipulator 156 functions substantially the same as the surgical manipulator 10, as described above, except that there is no elbow control and elbow movement. Therefore, no compensation mechanism is necessary. The gripper control for the gripper 26 of the surgical manipulator 156 is identical to the control described above with respect to the surgical manipulator 10. The wrist control for the internal wrist 24 of the surgical manipulator 156 is identical to the control described above with respect to the surgical manipulator 10. The surgical manipulator 156 may include a pivot ring 168 positioned about the main shaft 16 that allows the surgeon to push and pull the surgical manipulator 156, defining a degree of freedom, and to pivot the surgical manipulator 156 about the pivot ring 168, defining another degree of freedom.

FIGS. 17-27 illustrate another construction of a dexterous surgical manipulator 210 including an internal working end 212 and an external control interface 214 connected to the internal working end 212 by a main shaft 216. A center line F' is defined along the center of the surgical manipulator 10, as shown. The main shaft 216 is rigid and is formed of a suitable rigid material, such as carbon fiber or stainless steel and has a diameter of approximately 4 mm. The internal working end 212 also preferably has a diameter, measured perpendicular to the center line F', of approximately 4 mm. In other constructions, the size of the surgical manipulator 210 may be scaled as desired. Furthermore, a length of the main shaft 216 may be chosen to suit a particular application, as desired.

With particular reference to FIGS. 18-22, the internal working end 212 includes an internal elbow joint 218 adjacent the main shaft 216, an internal forearm 220 adjacent the internal elbow joint 218, an internal wrist 224 positioned adjacent the internal forearm 220, an internal wrist joint 222 positioned between the internal forearm 220 and the internal wrist 224, and a gripper 226 positioned adjacent the internal wrist 224 including a first gripper finger 228 and a second gripper finger 230.

The first gripper finger 228 includes a first gripper pulley 232 for receiving a first drive cable 236, and the second gripper finger 230 includes a second gripper pulley 234 for receiving a second drive cable 238, as will be described in greater detail below. In the illustrated construction, the pulleys 232, 234 are generally circular or semi-circular shaped surfaces having a groove therein for receiving the respective cable 236, 238 thereabout, as shown in FIGS. 20-22. In other constructions, the pulleys described herein may have other suitable shapes and configurations.

The first gripper finger 228 is pivotably coupled to the internal wrist 224 by a gripper pivot pin 242, and the second gripper finger 230 is pivotably coupled to the internal wrist 224 by the gripper pivot pin 242, which defines a gripper pivot axis A' (FIG. 18). An aperture 240 passing through the first and second gripper fingers 228, 230 and the internal wrist 224 receives the gripper pivot pin 242. The first and second gripper pulleys 232, 234 are centered about the gripper pivot axis A'. The first and second gripper fingers 228, 230 and the internal wrist 224 are pivotably coupled by the pivot pin 242.

The internal forearm 220, positioned adjacent the internal wrist 224 at a first axial end, is a generally cylindrical structure. The internal forearm 220 and the internal wrist 224 are pivotably coupled by a wrist pivot pin 250 defining a wrist pivot axis B'. The internal wrist joint 222 is generally defined by the internal wrist 224 being pivotably connected to the internal forearm 220 by way of the wrist pivot pin 250.

The internal forearm 220 includes first cable passages 256 (FIG. 19) and second cable passages (not shown) for receiving the first and second drive cables 236, 238, respectively. The second cable passages are generally mirror images of the first cable passages 56 positioned on an opposite side of the internal forearm 220. The cable passages 56 axially, substantially parallel with the center line F, between a first axial end adjacent the internal wrist 240 and a second axial end adjacent the internal elbow joint 218.

With particular reference to FIG. 18, the elbow joint 218 includes the main shaft 216 pivotably coupled to the internal forearm 220 by a first elbow pivot pin 262 defining a first elbow pivot axis C', providing the elbow joint 218 with a first degree of freedom. The elbow joint 218 also includes the main shaft 216 pivotably coupled to the internal forearm 220 by a second elbow pivot pin 266 defining a third elbow pivot axis E', providing the elbow joint 218 with a second degree of freedom. The second elbow pivot pin 266 is substantially perpendicular to the first elbow pivot pin 262. Likewise, the second elbow pivot axis E' is substantially perpendicular to the first elbow pivot axis C'.

Figure 24:
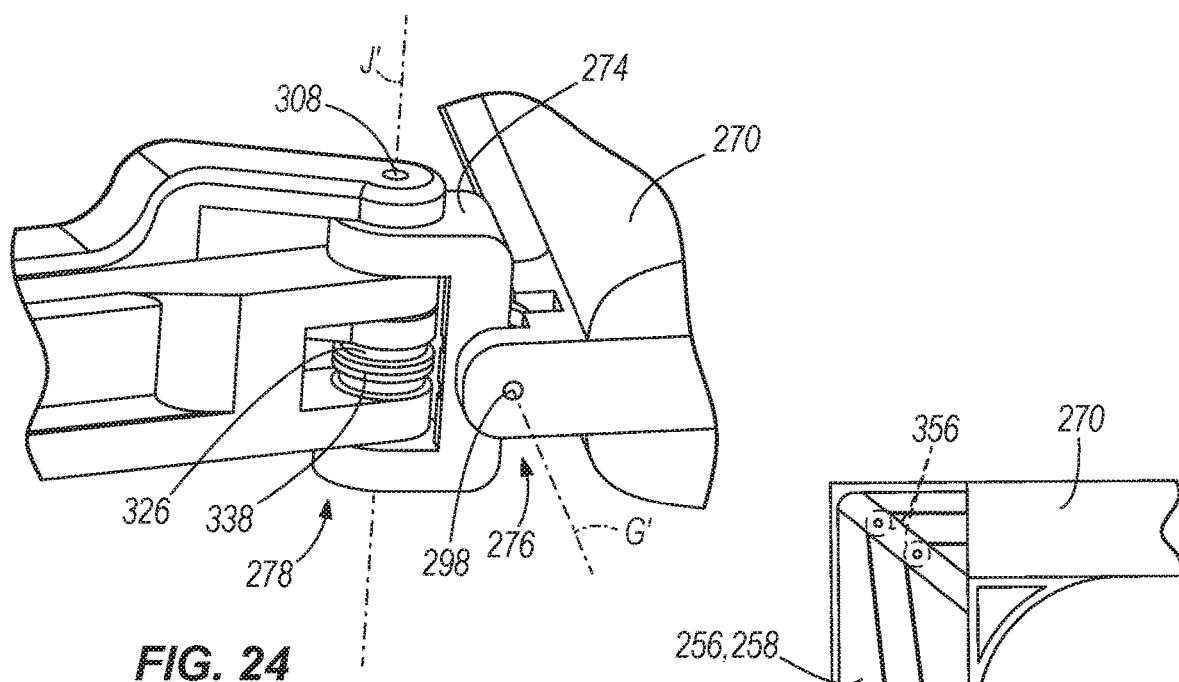
FIG. 24 is an enlarged view of the a portion of the control interface of FIG. 23.
Figure 25:
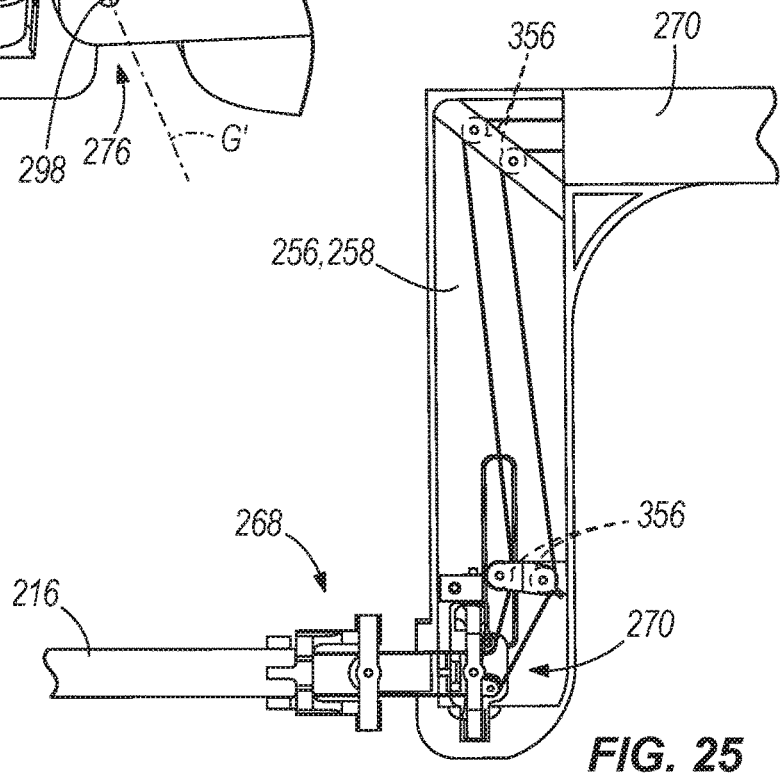
FIG. 25 is an enlarged view of a portion of the control interface of the surgical manipulator of FIG. 17.
Figure 26:
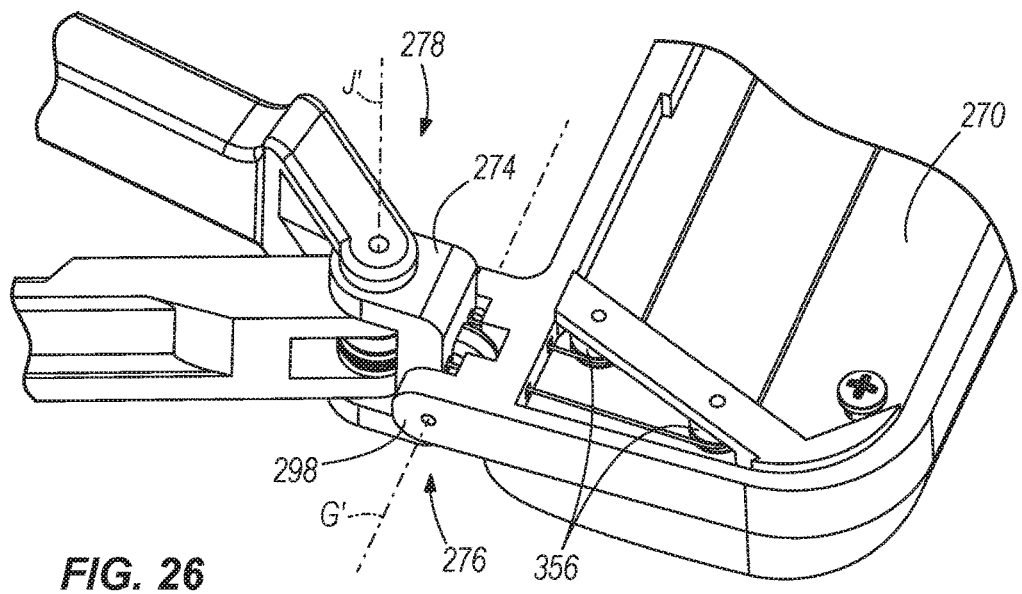
FIG. 26 is an enlarged view of another portion of the control interface of the surgical manipulator of FIG. 17.
Figure 27:
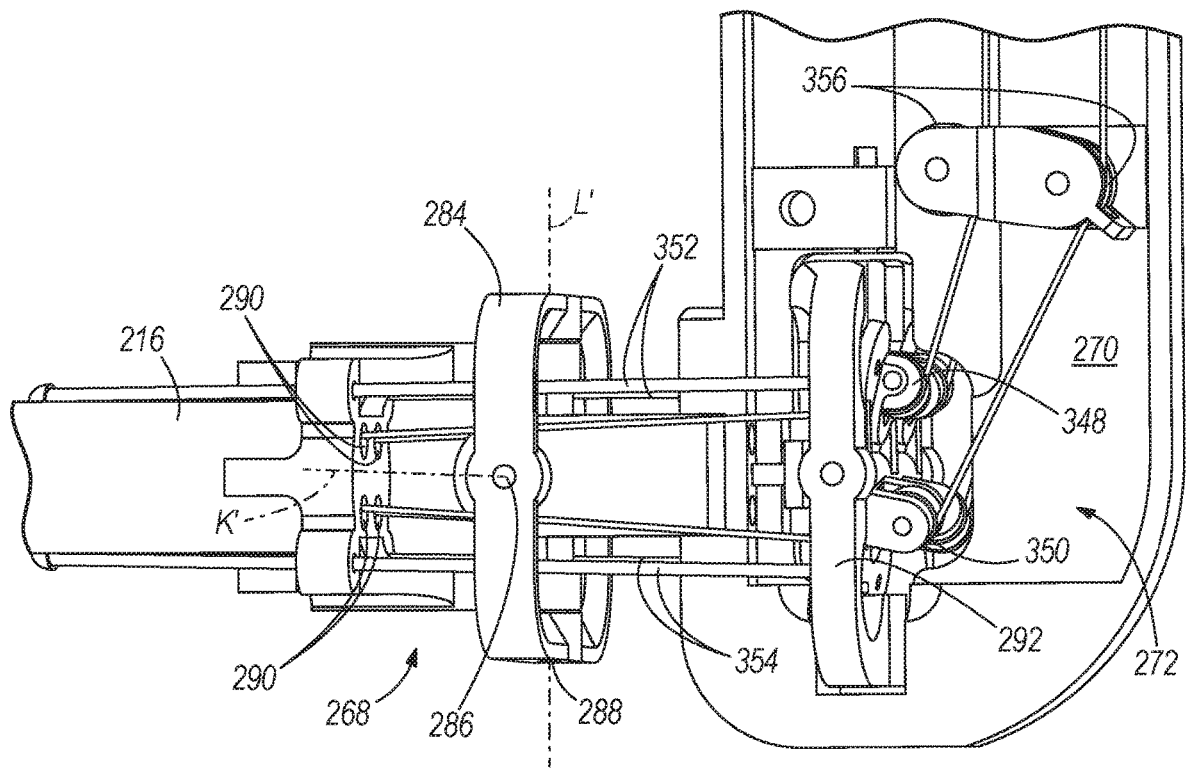
FIG. 27 is an enlarged view of another portion of the control interface of the surgical manipulator of FIG. 17.

With reference to FIGS. 23-29, the external control interface 214 includes an external elbow 268 (FIG. 27) coupled to an end of the main shaft 216 opposite the internal working end 212, an external forearm 270 coupled to the external elbow 268, a compensation mechanism 272 located in the external forearm 270 proximate the external elbow 268, an external wrist 274 coupled to the external forearm 274, a wrist joint 276 between the external forearm 270 and the external wrist 274, a user control 280 coupled to the external wrist 274 and a finger control joint 278 between the user control 280 and the external wrist 274. The external control interface 214 includes a plurality of idler pulleys 356 for directing the first and second cables 236, 238 substantially along the center line F (FIGS. 25-27).

With particular reference to FIG. 27, the external elbow 268 includes an elbow piece 284 fixedly coupled to the main shaft 216. The elbow piece 284 is pivotably coupled to the external forearm 270 by a first external elbow pin 286, thus defining a first degree of freedom of movement of the external elbow 268. The first external elbow pin 286 defines a first external elbow pivot axis K'. The elbow piece 284 is also coupled to the external forearm 270 by a second external elbow pin 288 that extends substantially perpendicular to the first external elbow pin 286. The second external elbow pin 288 defines a second external elbow pivot axis L', which is substantially perpendicular to the first external elbow pivot axis K'. Thus, the external elbow 268 has a first degree of freedom defined by the first external elbow pin 286 and a second degree of freedom defined by the second external elbow pin 288.

The external elbow 268 includes openings 290 extending generally axially, substantially parallel with the center line F, further defining the first and second cable passages 256, 258. The external forearm 270 also includes passages extending generally axially, substantially parallel with the center line F, further defining the first and second cable passages 256, 258.

The compensation mechanism 272 is best illustrated in FIG. 27 and includes a gimbaled plate 292 supporting pulleys 348, 350 for redirecting the cables 236, 238 from the external elbow 268 to the external forearm 270. The compensation mechanism 272 also includes pull rods 352, 354 coupled to the gimbaled plate 292 and to the main shaft 216. Movement of the external elbow 268 pushes and pulls the rods 352, 354 with respect to the exterior forearm 270, which pivots the gimbaled plate 292 to move the pulleys 348, 350, respectively. Moving the pulleys increases or decreases the path length of the respective cables 236, 238, effectively pulling or giving slack to the cables, which adjusts the gripper 226 and internal wrist 224 to compensate for movements in the external elbow 268.

With reference to FIG. 24, the external forearm 270 is pivotably coupled to the external wrist 274 by an external wrist pin 298 defining an external wrist pivot axis G'. The wrist joint 276 is generally defined by the external forearm 270 being pivotably coupled to the external wrist 274 by the external wrist pin 298. The external wrist 274 is pivotably coupled to the external forearm 270 at one end and at an opposite end is pivotably coupled to a first gripper lever 310 and a second gripper lever 312 by an external gripper pin 308, defining an external lever pivot axis J'. Each of the first and second gripper levers 310, 312 are independently pivotable with respect to the external wrist 274. The first gripper lever 310 includes a pulley 326 for receiving the first drive cable 236 thereabout, and the second gripper lever 312 includes a pulley 338 for receiving the second drive cable 238 thereabout. The first gripper lever 310 includes a termination area 328 in which the first drive cable 236 is terminated and secured. The second gripper lever 312 includes a termination area 340 in which the second drive cable 238 is terminated and secured. When the first gripper lever 310 is pivoted about the lever pivot axis J', the pulley 326 pulls the first drive cable 236 to actuate the first gripper finger 228. When the second gripper lever 312 is pivoted about the lever pivot axis J', the pulley 338 pulls the second drive cable 238 to actuate the second gripper finger 230.

When the external wrist 274 is pivoted about the axis G' in a first direction, the first drive cable 236 is pulled and the second drive cable 238 is released, causing the internal wrist joint 222 to rotate in a first direction. When the external wrist 274 is pivoted about the axis G' in a second direction opposite the first direction, the second drive cable 238 is pulled and the first drive cabled 236 is released, causing the internal wrist joint 222 to rotate in a second direction opposite the first direction, as shown in FIG. 21.

In other constructions, an external control interface may be linked to a computer, which receives input signals from the external control interface, translates the input signals into output signals, and transfers the output signals to an internal working end positioned remotely from the external control interface. Thus, the external control interface is not mechanically, but electronically, linked to the internal working end. Therefore, the term, "linked," as used herein, can include both mechanical and electrical linkages.

A surgical manipulator includes an internal working end and an external control interface for controlling the internal working end, the external control interface including first and second levers being pivotable about an axis and defining a grip. The surgical manipulator also includes a main shaft coupling the external control interface to the internal working end. The external control interface, the main shaft and the internal working end define a centerline. The grip is positioned between the axis and the internal working end with respect to the centerline.

A surgical manipulator includes an internal working end and an external control interface for controlling the internal working end, the external control interface including first and second levers being pivotable about an axis and defining a grip. The grip is positioned between the internal working end and the axis.

A surgical manipulator includes an internal working end having an internal joint and an external control interface linked to the internal working end for controlling the internal working end. The external control interface includes first and second levers defining a grip, and an external joint pivotable about an external axis. The external joint is linked to the internal joint such that the orientation of the internal joint depends on the orientation of the external joint. The external axis intersects the grip.

Furthermore, the internal joint is pivotable about an internal axis. The surgical manipulator also includes a gripper associated with the internal working end for grasping an object, the gripper pivotable about an internal gripper axis. The gripper axis is substantially perpendicular to the internal axis. The first and second levers are pivotable about an external gripper axis for controlling the position of the gripper, and a main shaft operably and mechanically couples the external control interface to the internal working end.

A surgical manipulator includes an internal working end having an internal joint, and an external control interface operably coupled to the internal working end for controlling the internal working end. The external control interface includes first and second levers defining a spherical grip volume between and including the first and second levers, and an external joint linked to the internal joint for controlling the internal joint. The external joint is positioned substantially within the spherical grip volume.

A surgical manipulator includes an internal working end having an internal joint and a gripper for grasping an object, and an external control interface linked to the internal working end for controlling the internal working end. The external control interface includes first and second levers linked to the gripper for controlling the gripper, and an external joint linked to the internal joint for controlling the internal joint. The external joint is positioned substantially between the first and second levers.

A surgical manipulator includes an internal working end having a first joint, an external control end having a second joint, and a drive cable extending between the internal working end and the external control end. The surgical manipulator also includes a sleeve housing the drive cable. The sleeve is operably coupled between the first and second joints such that movement of the second joint causes movement of the first joint by way of the sleeve.

A surgical manipulator includes an internal working end having an internal forearm pivotably coupled to a gripper for grasping an object, and an external control interface including an external forearm coupled to a user control for controlling the gripper. The surgical manipulator also includes a main shaft coupling the external control interface to the internal working end, the main shaft having a first end and a second end and being pivotably coupled to the internal forearm at the first end and pivotably coupled to the external forearm at the second end. The user control is pivotable with respect to the external forearm and defines a first angle with respect to the external forearm. The external forearm is pivotable with respect to the main shaft and defines a second angle with respect to the main shaft. The internal forearm is pivotable with respect to the main shaft and defines a third angle with respect to the main shaft. The gripper is pivotable with respect to the internal forearm and defines a fourth angle with respect to the internal forearm. The first and second angles are controllable by a user. The external control interface is linked to the internal working end for controlling the internal working end such that the fourth angle is dependent upon both the first and second angles.

A method of manipulating an object in a patient includes inserting a surgical tool through a lumen in the patient and moving the surgical tool toward the object. The surgical tool includes a shaft defining a longitudinal axis and having a first end and a second end, an internal forearm coupled to the first end of the shaft, an external forearm coupled to the second end of the shaft. The method also includes moving the internal forearm in a transverse direction with respect to the longitudinal axis forming a first angle having a first magnitude with respect to the longitudinal axis by moving the external forearm in the transverse direction and forming a second angle having substantially the same first magnitude with respect to the longitudinal axis.

A method of manipulating an object in a patient includes inserting a surgical tool through a lumen in the patient and moving the surgical tool toward the object. The surgical tool includes a shaft having a first end and a second end, a first joint coupled to the first end of the shaft, an internal forearm having a first end and a second end, the first end of the internal forearm coupled to the first joint, a second joint coupled to the second end of the internal forearm, an internal wrist having a first end and a second end, the first end of the internal wrist coupled to the second joint, a gripper coupled to the second end of the internal wrist, a third joint coupled to the second end of the shaft, an external forearm having a first end and a second end, the first end of the external forearm coupled to the third joint, a fourth joint coupled to the second end of the external forearm, an external wrist having a first end and a second end, the first end of the external wrist coupled to the fourth joint, a fifth joint coupled to the second end of the external wrist, a sixth joint coupled to the fifth joint, a first lever, and a second lever. The method also includes manually moving one of the external forearm, the external wrist, the first lever, and the second lever, determining a magnitude and a direction of the movement of the one of the external forearm, the external wrist, the first lever, and the second lever, and communicating the magnitude and the direction of the movement of the one of the external forearm, the external wrist, the first lever, and the second lever to automated means that automatically translate the magnitude and the direction into movement of one of the internal forearm, the internal wrist, and the gripper.

A device includes a first end and a second end having a control interface for controlling the first end, the control interface including first and second levers being pivotable about an axis and defining a grip. The device also includes a main shaft coupling the control interface to the first end. The control interface, the main shaft and the first end define a centerline. The grip is positioned between the axis and the first end with respect to the centerline.

A device includes a first end and a control interface for controlling the first end, the control interface including first and second levers being pivotable about an axis and defining a grip. The grip is positioned between the first end and the axis.

A device includes a first end having a first joint and a control interface linked to the first end for controlling the first end. The control interface includes first and second levers defining a grip, and a second joint pivotable about a first axis. The second joint is linked to the first joint such that the orientation of the first joint depends on the orientation of the second joint. The first axis intersects the grip.

Thus, the invention provides, among other things, a dexterous surgical manipulator having an intuitive user interface. Various features and advantages of the invention are set forth in the following claims.

What is claimed is:

1. A surgical manipulator, comprising:
   an internal working end having an internal joint; and
   an external control interface linked to the internal working end for controlling the internal working end, the external control interface including:
   a first lever and a second lever that together define a grip volume for a surgeon's hand when gripping and operating the first lever and the second lever, wherein at least one of the first lever and the second lever is pivotable about a first pivot axis (J), and
   an external wrist joint linked to the internal joint for controlling the internal joint;

wherein the external wrist joint is positioned at least substantially within the grip volume, wherein the external wrist joint includes a second pivot axis (H) and a third pivot axis (G) that are offset from one another, the second pivot axis (H) being disposed between the first pivot axis (J) and the third pivot axis (G);

wherein the first lever, the second lever, and the first pivot axis (J) together are rotatable about the third pivot axis (G), and a drive cable coupled between the internal working end and the control interface for mechanically linking the internal working end and the control interface, wherein the external wrist joint includes a pulley about which the drive cable is disposed, the pulley defining the third pivot axis.

2. The surgical manipulator of claim 1, wherein the grip volume is a spherical grip volume that is defined by distal end portions of both the first and second levers.

3. The surgical manipulator of claim 1, wherein the first lever and the second lever are substantially the same shape and size and mirror one another across a centerline (F) that extends from the first pivot axis toward the internal working end.

4. The surgical manipulator of claim 1, wherein the grip volume is substantially between the first pivot axis and the internal working end.

5. The surgical manipulator of claim 1, further comprising a cable box in which an end of the drive cable is secured, wherein the first lever is coupled to the cable box by a link.

6. The surgical manipulator of claim 1, further comprising:
an internal elbow joint having one degree of freedom; and
an external elbow joint having one degree of freedom;
wherein the external elbow joint is mechanically coupled to the internal elbow joint for mechanically controlling the internal elbow joint.

7. The surgical manipulator of claim 1, further comprising a support member to which both the first and second levers are coupled, wherein the first pivot axis extends through the support member.

8. The surgical manipulator of claim 7, wherein the support member is pivotable about the third pivot axis (G).

9. A surgical manipulator, comprising:
an internal working end having an internal joint;
an external control interface linked to the internal working end for controlling the internal working end, the external control interface including:
a first lever and a second lever that together define a grip volume for a surgeon's hand when gripping and operating the first lever and the second lever, wherein at least one of the first lever and the second lever is pivotable about a first pivot axis (J), and
an external wrist joint linked to the internal joint for controlling the internal joint;
wherein the external wrist joint is positioned at least substantially within the grip volume, wherein the external wrist joint includes a second pivot axis (H) and a third pivot axis (G) that are offset from one another, the second pivot axis (H) being disposed between the first pivot axis (J) and the third pivot axis (G);
wherein the first lever, the second lever, and the first pivot axis (J) together are rotatable about the third pivot axis (G);
a drive cable coupled between the internal working end and the control interface for mechanically linking the internal working end and the control interface; and a cable box in which an end of the drive cable is secured, wherein the first lever is coupled to the cable box by a link,
wherein the link includes a first end pivotably connected to the first lever and a second end pivotably connected to the cable box.

10. The surgical manipulator of claim 9, wherein the external wrist joint includes a pulley about which the drive cable is disposed, the pulley defining the third pivot axis.

11. The surgical manipulator of claim 9, wherein the grip volume is a spherical grip volume that is defined by distal end portions of both the first and second levers.

12. The surgical manipulator of claim 9, wherein the first lever and the second lever are substantially the same shape and size and mirror one another across a centerline (F) that extends from the first pivot axis toward the internal working end.

13. The surgical manipulator of claim 9, wherein the grip volume is substantially between the first pivot axis and the internal working end.

14. The surgical manipulator of claim 9, further comprising:
an internal elbow joint having one degree of freedom; and
an external elbow joint having one degree of freedom;
wherein the external elbow joint is mechanically coupled to the internal elbow joint for mechanically controlling the internal elbow joint.

15. The surgical manipulator of claim 9, further comprising a support member to which both the first and second levers are coupled, wherein the first pivot axis extends through the support member.

16. The surgical manipulator of claim 15, wherein the support member is pivotable about the third pivot axis (G).

17. A surgical manipulator, comprising:
an internal working end having an internal joint; and
an external control interface linked to the internal working end for controlling the internal working end, the external control interface including:
a first lever and a second lever that together define a grip volume for a surgeon's hand when gripping and operating the first lever and the second lever, wherein at least one of the first lever and the second lever is pivotable about a first pivot axis (J), and
an external wrist joint linked to the internal joint for controlling the internal joint;
wherein the external wrist joint is positioned at least substantially within the grip volume, wherein the external wrist joint includes a second pivot axis (H) and a third pivot axis (G) that are offset from one another, the second pivot axis (H) being disposed between the first pivot axis (J) and the third pivot axis (G);
wherein the first lever, the second lever, and the first pivot axis (J) together are rotatable about the third pivot axis (G);
an internal elbow joint having one degree of freedom;
an external elbow joint having one degree of freedom;
wherein the external elbow joint is mechanically coupled to the internal elbow joint for mechanically controlling the internal elbow joint;
a drive cable mechanically coupling the external wrist joint to the internal wrist joint for translation of movement therebetween; and
a sleeve disposed about the drive cable and mechanically coupling the external elbow joint to the internal elbow joint for translation of movement therebetween.

18. The surgical manipulator of claim 17, wherein the grip volume is a spherical grip volume that is defined by distal end portions of both the first and second levers.

19. The surgical manipulator of claim 17, wherein the first lever and the second lever are substantially the same shape and size and mirror one another across a centerline (F) that extends from the first pivot axis toward the internal working end.

20. The surgical manipulator of claim 17, wherein the grip volume is substantially between the first pivot axis and the internal working end.

* * * * *